US012367953B1

(12) United States Patent
Babu et al.

(10) Patent No.: US 12,367,953 B1
(45) Date of Patent: Jul. 22, 2025

(54) APPARATUS AND A METHOD FOR THE GENERATION OF A MEDICAL REPORT

(71) Applicant: Anumana, Inc., Cambridge, MA (US)

(72) Inventors: Melwin Babu, Thissur (IN); Rakesh Barve, Bengaluru (IN); Sravan Kumar Lalam, Bangalore (IN)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/798,021

(22) Filed: Aug. 8, 2024

(51) Int. Cl.
*G16H 15/00* (2018.01)
*G16H 10/60* (2018.01)

(52) U.S. Cl.
CPC .............. *G16H 15/00* (2018.01); *G16H 10/60* (2018.01)

(58) Field of Classification Search
CPC ................................ G16H 15/00; G16H 10/60
USPC .......................................................... 705/2–3
See application file for complete search history.

(56) References Cited

U.S. PATENT DOCUMENTS

| | | | |
|---|---|---|---|
| 10,482,116 B1 * | 11/2019 | Manchala | H04L 65/403 |
| 10,929,451 B1 * | 2/2021 | Manchala | G06F 16/345 |
| 11,056,227 B2 * | 7/2021 | Sreenivasan | G06T 7/0012 |
| 12,008,332 B1 * | 6/2024 | Gardner | G06F 16/345 |
| 2018/0329993 A1 * | 11/2018 | Bedadala | G06F 16/90332 |
| 2019/0362835 A1 * | 11/2019 | Sreenivasan | G06N 3/044 |
| 2020/0073982 A1 * | 3/2020 | Kolluri Venkata Sesha | G06F 11/3082 |
| 2020/0334416 A1 * | 10/2020 | Vianu | G06V 10/764 |
| 2020/0372055 A1 * | 11/2020 | Joko | G06F 40/268 |
| 2023/0092027 A1 * | 3/2023 | Bian | G16H 50/20 382/128 |
| 2023/0386646 A1 * | 11/2023 | Tanwani | G06V 10/806 |
| 2023/0418981 A1 * | 12/2023 | Ward | G06F 21/6254 |
| 2024/0029848 A1 * | 1/2024 | Gupta | G16H 15/00 |
| 2024/0212812 A1 * | 6/2024 | Vidyashankar Keresanthe | G16H 30/40 |
| 2024/0296924 A1 * | 9/2024 | Singh | G10L 15/26 |

FOREIGN PATENT DOCUMENTS

| | | | | |
|---|---|---|---|---|
| CN | 112992308 A | * | 6/2021 | G06N 20/00 |
| CN | 117352121 A | | 1/2024 | |
| WO | WO-2020214683 A1 | * | 10/2020 | G06N 3/044 |

(Continued)

OTHER PUBLICATIONS

Vinithavn; Medical Report Generation Using Deep Learning; Analytics Vidhya, Dec. 7, 2020.

(Continued)

*Primary Examiner* — Michael Tomaszewski
(74) *Attorney, Agent, or Firm* — Caldwell Intellectual Property Law

(57) ABSTRACT

An apparatus for the generation of a medical report is disclosed. The apparatus includes at least processor and a memory communicatively connected to the processor. The memory instructs the processor to receive a user query. The memory instructs the processor to receive a user profile comprising a plurality of medical tests. The memory instructs the processor to generate testing data as a function of the plurality of medical tests using an encoder. The memory instructs the processor to generate textual data that is representative of the testing data using a querying transformer model (Q-former). The memory instructs the processor to generate a medical report as a function of the user query and the textual data using a report large language model (LLM).

20 Claims, 11 Drawing Sheets

(56) References Cited

FOREIGN PATENT DOCUMENTS

WO     WO-2023026146 A1 *   3/2023     ............. G06N 20/00
WO     WO-2024145110 A1 *   7/2024     ............. G16H 15/00

OTHER PUBLICATIONS

Wenliang et al.;InstructBLIP: Towards General-purpose Vision-Language Models with Instruction Tuning; Jun. 15, 2023.
Rafallov et al.; Direct Preference Optimization: Your Language Model is Secretly a Reward Model; Jul. 29, 2024.

* cited by examiner

APPARATUS AND A METHOD FOR THE GENERATION OF A MEDICAL REPORT

FIELD OF THE INVENTION

The present invention generally relates to the field of medical technology. In particular, the present invention is directed to an apparatus and a method for the generation of a medical report.

BACKGROUND

The generation of medical reports is a critical task in healthcare that facilitates the communication of diagnostic findings, interpretations, and clinical recommendations based on analyses of various medical tests, such as echocardiograms, electrocardiograms, and imaging studies. Generating medical reports is time-consuming and subject to human error. It can also lead to inconsistencies in report structure and content due to individual variations in training, experience, and subjective judgment among medical practitioners. Moreover, the increasing volume of medical data and the growing complexity of diagnostic tests have made the task even more challenging, underscoring the need for improved efficiency and standardization in the generation of medical reports. Recent advances in artificial intelligence, particularly in the field of natural language processing and computer vision, have led to the development of systems that can assist with or automate parts of the report generation process. Large language models (LLMs), such as transformer models, have shown promise in understanding and generating human-like text. However, integrating the heterogeneous data types inherent in medical diagnostics, such as numerical test results, visual imaging data, and textual descriptions, into a coherent and medically accurate report remains a technical challenge.

SUMMARY OF THE DISCLOSURE

In an aspect, an apparatus for the generation of a medical report is disclosed. An apparatus for the generation of a medical report is disclosed. The apparatus includes at least processor and a memory communicatively connected to the processor. The memory instructs the processor to receive a user query. The memory instructs the processor to receive a user profile comprising a plurality of medical tests. The memory instructs the processor to generate testing data as a function of the plurality of medical tests using an encoder. The memory instructs the processor to generate textual data that is representative of the testing data using a querying transformer model (Q-former). Generating the textual data comprises iteratively training the Q-former using transformer training data, wherein transformer training data comprises pairs of examples of testing data and examples of textual data. Additionally, generating the textual data comprises generating the textual data using the trained querying transformer model. The memory instructs the processor to generate a medical report as a function of the user query and the textual data using a report large language model (LLM).

In another aspect, a method for the generation of a medical report is disclosed. The method includes receiving, using at least a processor, a user query. The method includes receiving, using the at least a processor, a user profile comprising a plurality of medical tests. The method includes generating testing data as a function of the plurality of medical tests using an encoder. The method includes generating textual data that is representative of the testing data using a querying transformer model (Q-former). Generating the textual data comprises iteratively training the Q-former using transformer training data, wherein transformer training data comprises pairs of examples of testing data and examples textual data. Additionally, generating the textual data comprises generating the textual data using the trained querying transformer model. The method includes generate a medical report as a function of the user query and the textual data using a report large language model (LLM).

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

Figure 1A:
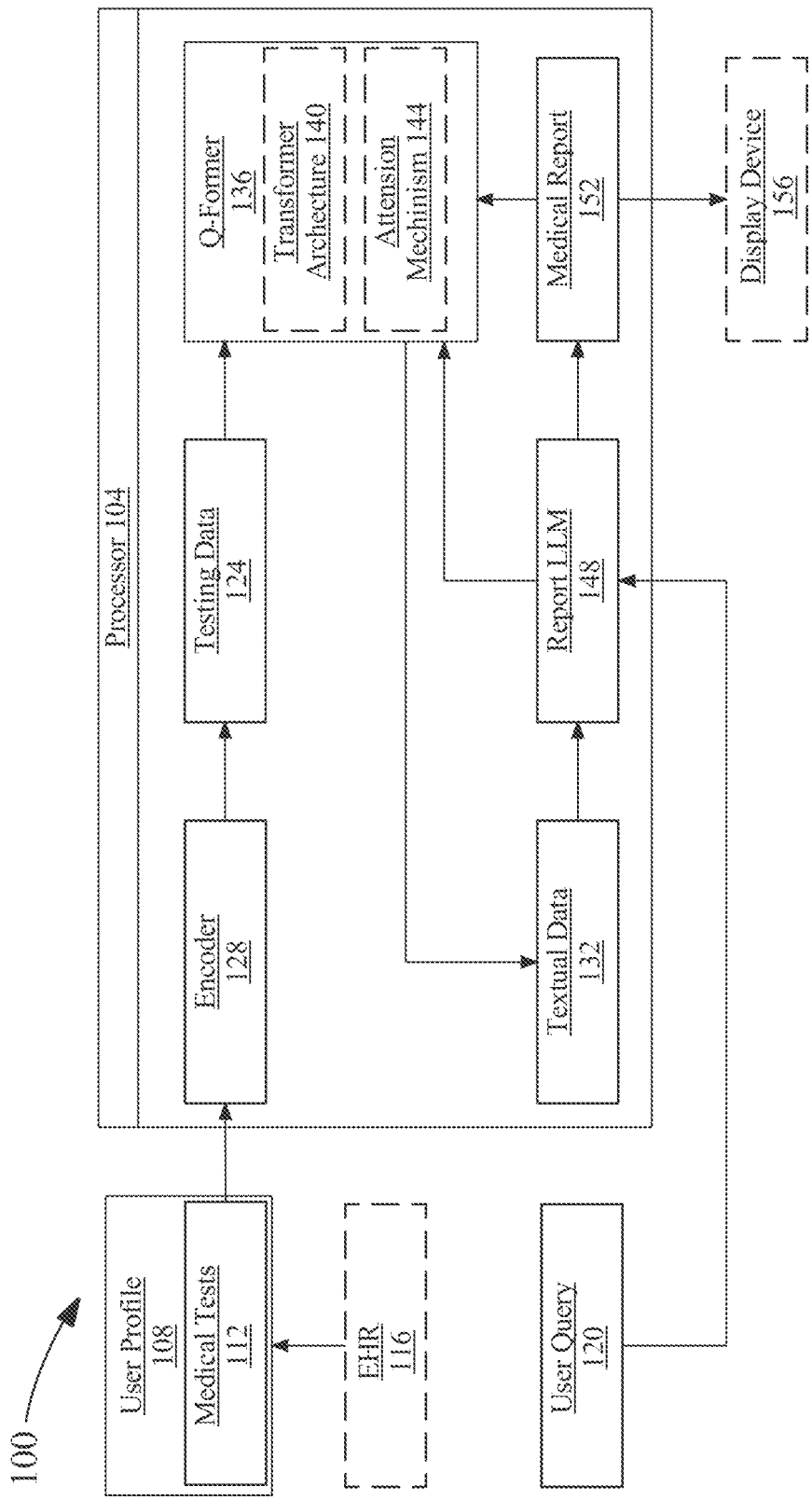
FIGS. 1A-D is a block diagram of an exemplary embodiment of an apparatus for the generation of a medical report.
Figure 1B:
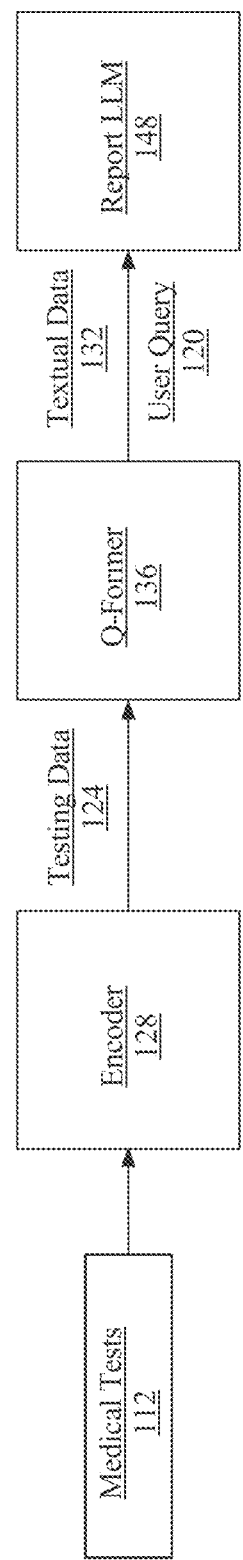
Figures 1C, 1D:
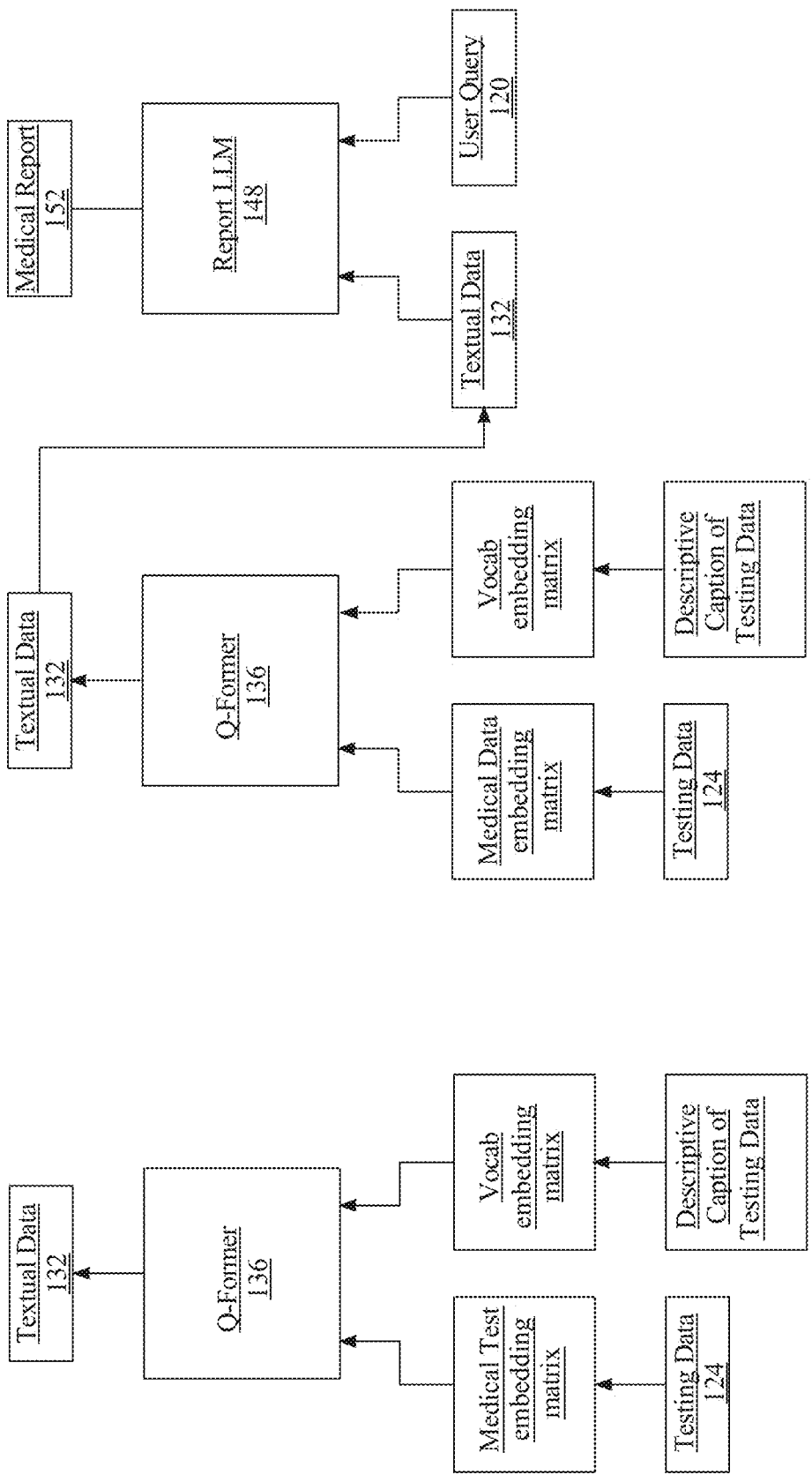

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to an apparatus and a method for the generation of a medical report. An apparatus for the generation of a medical report is disclosed. The apparatus includes at least processor and a memory communicatively connected to the processor. The memory instructs the processor to receive a user query. The memory instructs the processor to receive a user profile comprising a plurality of medical tests. The memory instructs the processor to generate testing data as a function of the plurality of medical tests using an encoder. The memory instructs the processor to generate textual data that is representative of the testing data using a querying transformer model (Q-former). Generating the textual data comprises iteratively training the Q-former using transformer training data, wherein transformer training data comprises examples of testing data as inputs correlated to examples of textual data as outputs. Additionally, generating the textual data comprises generating the textual data using the trained querying transformer model. The memory instructs the processor to generate a medical report as a function of the user query and the textual data using a report large language model (LLM). Exemplary embodiments illustrating aspects of the present disclosure are described below in the context of several specific examples.

Referring now to FIGS. 1A-D, an exemplary embodiment of an apparatus 100 for the generation of a medical report is illustrated. Apparatus 100 includes a processor 104. Processor 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented using a "shared nothing" architecture in which data is cached at the worker, in an embodiment, this may enable scalability of apparatus 100 and/or computing device.

With continued reference to FIG. 1A, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIGS. 1A-D, apparatus 100 includes a memory. Memory is communicatively connected to processor 104. Memory may contain instructions configuring processor 104 to perform tasks disclosed in this disclosure. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, apparatus, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example, and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, without limitation, via a bus or other facility for intercommunication between elements of a computing device. Communicative connecting may also include indirect connections via, for example, and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1A, processor 104 may be configured to receive a user profile 108 from a user. For the purposes of this disclosure, a "user profile" is a representation of information and/or data associated with a user. A user profile 108 may be made up of a plurality of user data. As used in the current disclosure, "user data" is information associated with the user. A user profile 108 may be created by a processor 104, a user, medical professional, or a third party. The user profile 108 may include but is not limited to any of the following personal information: age, weight, height, gender, geographical location, insurance information, medical history, marital status, familial medical history, medical tests and the like. User profile 108 may be provided by a user or a third party on behalf of a user, for instance and without limitation a physician, medical professional, nurse, hospice care worker, mental health professional, family member, and the like. User profile 108 may originate from a user questionnaire, graphical user interface (GUI), or any other suitable forum for gathering information regarding user data and medical tests 112. Persons skilled in the art, upon review of this disclosure in its entirety, will be aware of the various ways in which user profile 108 and/or medical tests 112 may be collected and provided to the system described herein.

With continued reference to FIG. 1A, a user profile 108 may include the results of a plurality of medical tests 112. As used in the current disclosure, "medical tests" are procedures or examinations conducted to detect, diagnose, or monitor diseases, disease processes, susceptibility, or potential risks to health. Medical tests 112 may cover a comprehensive range of diagnostics that involve various organs and systems within the human body, including but not limited to the heart, liver, lungs, brain, bones, pancreas, reproductive organs, skin, blood, digestive tract, and eyes. Additionally, medical tests 112 may include a range of diagnostics relating to the left atrium pulmonic valve, left ventricle, aorta/aortic root, pericardium/epicardium, mitral valve, interatrial septum, mass/thrombus, tricuspid valve, right atrium, left ventricle, aortic valve, inferior/superior vena cava, and the like. Medical tests 112 may include diagnostics that are used to test for a specific condition or disease within a user. This may include diseases/conditions such as pulmonary hypertension, hyperkalemia, LVEF, Left ventricular hypertrophy, coronary atherosclerosis, high blood pressure, coronary heart disease, First degree AV Block, Right Bundle, Branch Block, Left Axis Deviation, Prolonged QT interval, and the like. These tests are integral in evaluating overall health, pinpointing disease states, and guiding treatment decisions. In a non-limiting example, medical tests 112 may include cardiological assessments such as an echocardiogram, electrocardiogram, transthoracic echocardiogram, and stress echocardiogram; continuous monitoring like blood pressure monitoring and right heart catheterization (RHC); medical imaging tests including MRI, ultrasound, X-ray, and CT scans; laboratory tests such as blood profiles, hormone levels, and metabolic tests; biopsies for histological analysis; and specialized tests like a Potassium test for electrolyte balance. The results of these tests can be presented in various forms, such as digital reports, printed documents, or integrated into electronic health records (EHRs). They may include quantitative data, like numerical values and metrics, qualitative results such as images and descriptive text, and interpretive summaries that provide insights into the patient's condition. These documents or records are vital for ongoing healthcare management, facilitating accurate diagnosis, and formulating tailored treatment strategies.

With continued reference to FIG. 1A, medical tests 112 may include a plurality of electrocardiogram (ECG) signals from a user. As used in the current disclosure, a "electrocardiogram signal" is a signal representative of the electrical activity of the heart. The ECG signals may consist of several distinct waves and intervals, each representing a different phase of the cardiac cycle. These waves may include the P-wave, QRS complex, T wave, U wave, and the like. The P-wave may represent atrial depolarization (contraction) as the electrical impulse spreads through the atria. The QRS complex may represent ventricular depolarization (contraction) as the electrical impulse spreads through the ventricles. The QRS complex may include three waves: Q wave, R wave, and S wave. The T-wave may represent ventricular repolarization (recovery) as the ventricles prepare for the next contraction. The U-wave may sometimes be present after the T wave, it represents repolarization of the Purkinje fibers. The intervals between these waves provide information about the duration and regularity of various phases of the cardiac cycle. The ECG signals can be used to help diagnose various heart conditions, such as arrhythmias, myocardial infarction (heart attack), conduction abnormalities, electrolyte imbalances, coronary heart disease, and the like. In an embodiment, each sensor may generate an individual ECG signals.

Continuing with reference to FIG. 1A, medical tests 112 may include a plurality of echocardiogram (ECHO) scans from a user. As described herein, an "echocardiogram" refers to an ultrasound image or recording that depicts the motion of the heart's chambers and valves. The echocardiogram scans can capture several key elements of cardiac function, including chamber size, wall thickness, and motion of the heart's valves. These images may include views such as the parasternal long and short axes, apical views, and subcostal views, each offering different perspectives of the heart. The echocardiogram is instrumental in assessing the pumping capacity of the heart and can help in diagnosing conditions such as heart failure, valve diseases, myocardial disease, and congenital heart defects. The scans can also measure the ejection fraction, which indicates how well the heart is pumping blood. In an embodiment, each sensor may generate individual echocardiogram scans, providing real-time insights into the heart's structural and functional attributes.

With continued reference to FIG. 1A, medical tests 112 may be extracted from a user using at least a sensor. As used in this disclosure, a "sensor" is a sensor device that produces an electrical output signal for the purpose of sensing and monitoring biological events or changes in its environment. In some cases, the sensor may include one or more processors that perform one or more processing steps as described in this disclosure. In some cases, the sensor may include, without limitation, a temperature sensor, EMG sensor, ECG machine, EKG machine, medical imaging device, pressure sensor, and the like thereof. In some embodiments, without limitation, the sensor may include a physical sensor, wherein the physical sensor is a device that measures a physical quantity. In some cases, the sensor may convert physical quantity into an output signal which can be read by processor 104. Data detected by sensor may include, but is not limited to, electrocardiogram signals, echocardiogram signals, heart rate, blood pressure, electrical signals related to the heart, and the like. In one or more embodiments, and without limitation, sensor may include a plurality of sensors. At least a sensor may include an ECG machine. In one or more embodiments, and without limitation, sensor may include one or more electrodes, and the like. Electrodes used for an electrocardiogram (ECG) are small sensors or conductive patches that are placed on specific locations on the body to detect and record the electrical signals generated by the heart. The electrodes serves as the interface between the body and the ECG machine, allowing for the measurement and recording of the heart's electrical activity. A plurality of sensors may include 10 electrodes used for a standard 12-lead ECG, placed in specific positions on the chest and limbs of the patient. Sensors may also include various lead systems including, 1-lead, 2-lead, 6-leads, 12, leads, standard limb leads, augmented limb leads, pectoral leads, and the like. These electrodes are typically made of a conductive material, such as metal or carbon, and are connected to lead wires that transmit the electrical signals to the ECG machine for recording. Proper electrode placement may be crucial to ensure accurate signal detection and recording. A number of electrodes used by an ECG machine may depend on a particular machine in use and may vary from a single electrode on a wearable device to twelve or more electrodes, or any number in between.

With continued reference to FIG. 1A, the plurality of sensors may be placed on each limb, wherein there may be at least one sensor on each arm and/or leg of the user. These sensors may be labeled I, II, III, V1, V2, V3, V4, V5, V6, and the like. For example, Sensor I may be placed on the left arm, Sensor II may be placed on the right arm, and Sensor III may be placed on the left leg. Additionally, a plurality of sensors may be placed on various portions of the patient's torso and chest. For example, a sensor V1 may be placed in the fourth intercostal space at both the right sternal borders and sensor V2 may be fourth intercostal space at both the left sternal borders. A sensor V3 may also be placed between sensors V2 and V4, halfway between their positions. Sensor V4 may be placed in the fifth intercostal space at the midclavicular line. Sensor V5 may be placed horizontally at the same level as sensor V4 but in the anterior axillary line. Sensor V6 may be placed horizontally at the same level as V4 and V5 but in the midaxillary line.

With continued reference to FIG. 1A, the plurality of sensors may include augmented unipolar sensors. These sensors may be labeled as aVR, aVL, and aVF. These sensors may be derived from the limb sensors and provide additional information about the heart's electrical activity. These leads are calculated using specific combinations of the limb leads and help assess the electrical vectors in different orientations. For example, aVR may be derived from Sensor II and Sensor III. In another example, aVL may be derived from sensor I and Sensor III. Additionally, aVF may be derived from Lead I and Lead II. The combination of limb sensors, precordial sensors, and augmented unipolar sensors allows for a comprehensive assessment of the heart's electrical activity in three dimensions.

With continued reference to FIG. 1A, a sensor may include a wearable device. As used in the current disclosure, a "wearable device" is a computing device that is designed to be worn on a user's body or clothing. The wearable device may be used to perform one or more medical tests 112 on the user. In embodiments, a wearable device may include a smart watch, smart ring, fitness tracking device, and the like. As used in the current disclosure, "wearable device data" is data collected by a wearable device. Wearable device data may include data and associated analysis corresponding to, for instance and without limitation, accelerometer data, pedometer data, gyroscope data, electrocardiography (ECG) data, electrooculography (EOG) data, bioimpedance data, blood pressure and heart rate monitoring, oxygenation data, biosensors, fitness trackers, force monitors, motion sensors, and the like.

With continued reference to FIG. 1A, a user profile 108 may be received by processor 104 via user input. For example, and without limitation, the user or a third party may manually input user profile 108 using a user interface, or a remote device, such as for example, a smartphone or laptop. The user profile 108 may additionally be generated using answers to a series of questions. The series of questions may be implemented using a chatbot, as described herein below. A chatbot may be configured to generate questions regarding any element of the user profile 108. In a non-limiting embodiment, a user may be prompted to input specific information or may fill out a questionnaire. In another embodiment, a user may be prompted to input specific information using drop down menus, check boxes, text fields, and the like. In an additional embodiment, a graphical user interface may display a series of questions to prompt a user for information pertaining to the user profile 108. The user profile 108 may be transmitted to processor 104, such as using a wired or wireless communication, as previously discussed in this disclosure. The user profile 108 can be retrieved from multiple sources third-party sources including the user's medical records, insurance records, family records, past user profiles 108, medical professional notes and observations, and the like. A user profile may be placed through an encryption process for security purposes.

With continued reference to FIG. 1A, processor 104 may receive a user profile 108 from a user database. In an embodiment, any past or present versions of any data disclosed herein may be stored within the user database including but not limited to the user profile 108, medical tests 112, user records, and the like. Processor 104 may be communicatively connected with user database. For example, in some cases, database may be local to processor 104. Alternatively or additionally, in some cases, database may be remote to processor 104 and communicative with processor 104 by way of one or more networks. Network may include, but not limited to, a cloud network, a mesh network, or the like. By way of example, a "cloud-based" system, as that term is used herein, can refer to a system which includes software and/or data which is stored, managed, and/or processed on a network of remote servers hosted in the "cloud," e.g., via the Internet, rather than on local severs or personal computers. A "mesh network" as used in this disclosure is a local network topology in which the infrastructure processor 104 connects directly, dynamically, and non-hierarchically to as many other computing devices as possible. A "network topology" as used in this disclosure is an arrangement of elements of a communication network. user database may be implemented, without limitation, as a relational database, a key-value retrieval database such as a NOSQL database, or any other format or structure for use as a database that a person skilled in the art would recognize as suitable upon review of the entirety of this disclosure. user database may alternatively or additionally be implemented using a distributed data storage protocol and/or data structure, such as a distributed hash table or the like. user database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

With continued reference to FIG. 1A, a user profile 108 and/or medical tests 112 may be received from one or more medical records. As used in the current disclosure, a "medical record" is a document that contains information regarding the user's medical history. Medical records may include data about any medical procedures, medical tests, medical images, observations of a medical professional, prescription history, diagnostic history, government records (i.e., birth certificates, social security cards, and the like), and the like of the user. Medical records may be identified using a web crawler. Medical records may include a variety of types of "notes" entered over time by a medical professional. Medical records may be converted into machine-encoded text using an optical character reader (OCR).

Still referring to FIG. 1A, in some embodiments, optical character recognition or optical character reader (OCR)

includes automatic conversion of images of written (e.g., typed, handwritten, or printed text) into machine-encoded text. In some cases, recognition of at least a keyword from an image component may include one or more processes, including without limitation optical character recognition (OCR), optical word recognition, intelligent character recognition, intelligent word recognition, and the like. In some cases, OCR may recognize written text, one glyph or character at a time. In some cases, optical word recognition May recognize written text, one word at a time, for example, for languages that use a space as a word divider. In some cases, intelligent character recognition (ICR) may recognize written text one glyph or character at a time, for instance by employing machine learning processes. In some cases, intelligent word recognition (IWR) may recognize written text, one word at a time, for instance by employing machine learning processes.

Still referring to FIG. 1A, in some cases, OCR may be an "offline" process, which analyses a static document or image frame. In some cases, handwriting movement analysis can be used as input for handwriting recognition. For example, instead of merely using shapes of glyphs and words, this technique may capture motions, such as the order in which segments are drawn, the direction, and the pattern of putting the pen down and lifting it. This additional information can make handwriting recognition more accurate. In some cases, this technology may be referred to as "online" character recognition, dynamic character recognition, real-time character recognition, and intelligent character recognition.

Still referring to FIG. 1A, in some cases, OCR processes may employ pre-processing of image components. Pre-processing process may include without limitation de-skew, de-speckle, binarization, line removal, layout analysis or "zoning," line and word detection, script recognition, character isolation or "segmentation," and normalization. In some cases, a de-skew process may include applying a transform (e.g., homography or affine transform) to the image component to align text. In some cases, a de-speckle process may include removing positive and negative spots and/or smoothing edges. In some cases, a binarization process may include converting an image from color or greyscale to black-and-white (i.e., a binary image). Binarization may be performed as a simple way of separating text (or any other desired image component) from the background of the image component. In some cases, binarization may be required for example if an employed OCR algorithm only works on binary images. In some cases, a line removal process may include the removal of non-glyph or non-character imagery (e.g., boxes and lines). In some cases, a layout analysis or "zoning" process may identify columns, paragraphs, captions, and the like as distinct blocks. In some cases, a line and word detection process may establish a baseline for word and character shapes and separate words, if necessary. In some cases, a script recognition process may, for example in multilingual documents, identify a script allowing an appropriate OCR algorithm to be selected. In some cases, a character isolation or "segmentation" process may separate signal characters, for example, character-based OCR algorithms. In some cases, a normalization process may normalize the aspect ratio and/or scale of the image component.

Still referring to FIG. 1A, in some embodiments, an OCR process will include an OCR algorithm. Exemplary OCR algorithms include matrix-matching process and/or feature extraction processes. Matrix matching may involve comparing an image to a stored glyph on a pixel-by-pixel basis. In some cases, matrix matching may also be known as "pattern matching," "pattern recognition," and/or "image correlation." Matrix matching may rely on an input glyph being correctly isolated from the rest of the image component. Matrix matching may also rely on a stored glyph being in a similar font and at the same scale as input glyph. Matrix matching may work best with typewritten text.

Still referring to FIG. 1A, in some embodiments, an OCR process may include a feature extraction process. In some cases, feature extraction may decompose a glyph into features. Exemplary non-limiting features may include corners, edges, lines, closed loops, line direction, line intersections, and the like. In some cases, feature extraction may reduce dimensionality of representation and may make the recognition process computationally more efficient. In some cases, extracted feature can be compared with an abstract vector-like representation of a character, which might reduce to one or more glyph prototypes. General techniques of feature detection in computer vision are applicable to this type of OCR. In some embodiments, machine-learning process like nearest neighbor classifiers (e.g., k-nearest neighbors algorithm) can be used to compare image features with stored glyph features and choose a nearest match. OCR may employ any machine-learning process described in this disclosure, for example machine-learning processes described with reference to FIGS. 5-7. Exemplary non-limiting OCR software includes Cuneiform and Tesseract. Cuneiform is a multi-language, open-source optical character recognition system originally developed by Cognitive Technologies of Moscow, Russia. Tesseract is free OCR software originally developed by Hewlett-Packard of Palo Alto, California, United States.

Still referring to FIG. 1A, in some cases, OCR may employ a two-pass approach to character recognition. The second pass may include adaptive recognition and use letter shapes recognized with high confidence on a first pass to recognize better remaining letters on the second pass. In some cases, two-pass approach may be advantageous for unusual fonts or low-quality image components where visual verbal content may be distorted. Another exemplary OCR software tool include OCRopus. OCRopus development is led by German Research Centre for Artificial Intelligence in Kaiserslautern, Germany. In some cases, OCR software may employ neural networks, for example neural networks as taught in reference to FIGS. 2, 4, and 5.

Still referring to FIG. 1A, in some cases, OCR may include post-processing. For example, OCR accuracy can be increased, in some cases, if output is constrained by a lexicon. A lexicon may include a list or set of words that are allowed to occur in a document. In some cases, a lexicon may include, for instance, all the words in the English language, or a more technical lexicon for a specific field. In some cases, an output stream may be a plain text stream or file of characters. In some cases, an OCR process may preserve an original layout of visual verbal content. In some cases, near-neighbor analysis can make use of co-occurrence frequencies to correct errors, by noting that certain words are often seen together. For example, "Washington, D.C." is generally far more common in English than "Washington DOC." In some cases, an OCR process may make use of a priori knowledge of grammar for a language being recognized. For example, grammar rules may be used to help determine if a word is likely to be a verb or a noun. Distance conceptualization may be employed for recognition and classification. For example, a Levenshtein distance algorithm may be used in OCR post-processing to further optimize results.

With continued reference to FIG. 1A, user profile 108 may be generated using a web crawler. A "web crawler," as used herein, is a program that systematically browses the internet for the purpose of Web indexing. The web crawler may be seeded with platform URLs, wherein the crawler may then visit the next related URL, retrieve the content, index the content, and/or measures the relevance of the content to the topic of interest. In some embodiments, processor 104 may generate a web crawler to compile the user profile 108 and medical tests 112. The web crawler may be seeded and/or trained with a reputable website, such as the user's medical provider's website, to begin the search. A web crawler may be generated by a processor 104. In some embodiments, the web crawler may be trained with information received from a user through a user interface. In some embodiments, the web crawler may be configured to generate a web query. A web query may include search criteria received from a user. For example, a user may submit a plurality of websites for the web crawler to search to extract user records, past user profiles 108, notes, and observations, based on criteria such as a time, location, and the like.

With continued reference to FIG. 1A, processor 104 may be configured to receive user profile 108 from an electronic health records (EHR) 116. As used in the current disclosure, "electronic health record" is a data structure which includes a collection of a health data associated with the user. As used in the current disclosure, "health data" refers to the collection of information related to a patient's health and healthcare. Health data may include elements of data regarding treatment records, medical history, laboratory results, radiology reports, medical records, clinical notes, and the like. An electronic health record (EHR) 116 may be a digital version of a patient's medical information that is stored and managed in a computerized system. It may be a comprehensive, longitudinal collection of a patient's health-related data that includes medical history, diagnoses, medications, treatment plans, test results, and other relevant health information. EHRs 116 may contain a wide range of patient information, including personal demographics, medical history, allergies, immunizations, medications, laboratory results, imaging reports, surgical procedures, and progress notes. This data may provide a complete overview of a patient's health and facilitates informed decision-making. EHRs 116 may include a patient's past and current medical conditions, surgeries, allergies, immunization records, medications, symptoms, medical observations, and any significant health events. EHRs 116 may additionally include a large amount of information regarding the patient's health background. This may include previous diagnosis, medical tests, medical imaging, and the like. EHRs may include documentation, observations, assessments, and treatment plans from medical professionals. This may include progress notes, discharge summaries, and other relevant clinical documentation. EHRs may include information related to prescribed medications, including dosage, frequency, symptoms, effect, and duration. EHRs may include test results, which may include laboratory test results, radiology reports, medical imaging reports, and other diagnostic imaging findings.

With continued reference to FIG. 1A, EHRs 116 may be received by processor 104 via user input. For example, and without limitation, the user or a third party may manually input EHRs 116 using a graphical user interface of processor 104 or a remote device, such as for example, a smartphone or laptop. EHRs 116 may additionally be generated via the answer to a series of questions. In a non-limiting embodiment, a user may be prompted to input specific information or may fill out a questionnaire. In an embodiment, a graphical user interface may display a series of questions to prompt a user for information pertaining to the EHRs 116. The EHRs 116 may be transmitted to processor 104, such as via a wired or wireless communication, as previously discussed in this disclosure.

With continued reference to FIG. 1A, processor 104 may be configured to receive a user profile 108 using an application programming interface (API). As used herein, an "application programming interface" is a set of functions that allow applications to access data and interact with external software components, operating systems, or microdevices, such as another web application or computing device. An API may define the methods and data formats that applications can use to request and exchange information. APIs enable seamless integration and functionality between different systems, applications, or platforms. An API may deliver a user profile 108 to apparatus 100 from a system/application that is associated with a user or other third-party custodian of user information. An API may be configured to query for web applications or other websites to retrieve a user profile 108 or other data associated with the user. An API may be further configured to filter through web applications according to a filter criterion. In this disclosure, "filter criterion" are conditions the web applications must fulfill in order to qualify for API. Web applications may be filtered based off these filter criteria. Filter criterion may include, without limitation, web application dates, web application traffic, web application types, web applications addresses, and the like. Once an API filters through web applications according to a filter criterion, it may select a web application. Processor 104 may transmit, through the API, user data include a user profile 108 to apparatus 100. API may further automatically fill out user entry fields of the web application with the user credentials in order to gain access to the user profile 108. Web applications may include, without limitation, a social media website, an online form, file scanning, email programs, third party websites, governmental websites, or the like.

With continued reference to FIG. 1A, processor 104 may be configured to preprocess a user profile 108. Preprocessing a user profile 108 may involve a series of steps to prepare and clean the data before it can be used for analysis, storage, or further processing. Preprocessing of the user profile 108 may include validating the user profile 108 to ensure that it is complete, accurate, and consistent. Processor 104 may check for any missing or erroneous information, and correct or flag such issues. Preprocessing a user profile 108 may involve cleaning the data associated with the user profile 108. This may include cleaning the data to remove any inconsistencies, outliers, duplicates, and the like. This can involve standardizing formats, dealing with missing values, and eliminating redundant or irrelevant information. In some embodiments, preprocessing the user profile 108 may include normalizing the data to bring it to a consistent format. For instance, standardize units of measurement (e.g., pounds to kilograms) or date formats. In some cases, preprocessing the user profile may include transforming the data into a suitable format for analysis or storage. This might include converting data into numerical values or encoding categorical variables. If the user profile 108 is collected from multiple sources, processor 104 may integrate the data into a unified dataset, mapping common identifiers to establish connections between different pieces of information. In the context of medical tests 112, preprocessing the user profile 108 may involve extracting specific health-related parameters or measurements, such as heart rate, blood pressure, chemical markers, ECG signals, EKG signals, and the like. In other cases, preprocessing the user profile 108 may include ensuring that sensitive personal and health information is properly anonymized and encrypted to protect user privacy.

With continued reference to FIG. 1A, processor 104 may be configured to extract a plurality of contextual data from the user profile 108. As used in the current disclosure, "contextual data" refers to additional information or details that provide a more comprehensive understanding of a current situation. This additional information may play a crucial role in interpreting and comprehending user profile 108 within a specific context. Contextual data proves indispensable for precise analysis, utilization, and the extraction of insights from a dataset. This contextual data can be directly pertinent to a particular scenario, event, or entity, furnishing the necessary background and details to grasp the data's significance in that specific context. On occasion, contextual data may be employed to establish the temporal context for a user query or dataset, encompassing timestamps, time of day, day of the week, or any other time-related details that elucidate when the data was generated or its relevance to a specific moment. This may encompass the chronological sequence or timing of events or queries. Moreover, a temporal context regarding the data can be gleaned in relation to recent test and lab results. Recent laboratory test results, imaging reports, pathology results, and other diagnostic data serve to contextualize the model. This contextualization empowers it to correlate symptoms with actual test findings. In an alternative scenario, the user's adherence or non-adherence to prior medical practitioner instructions can supply added context to the user profile. This may involve particulars of medication usage, dosages, frequency, and adherence to prescribed medication plans. A clear comprehension of the user's medication regimen is crucial for providing suitable advice and considering potential interactions. In certain instances, contextual data may encompass information about a user's dietary and lifestyle choices, such as dietary habits, exercise routines, smoking or alcohol consumption, sleep patterns, and stress levels. Lifestyle factors can furnish the model with additional context for user profile 108. For example, a user who excessively consumes alcohol or other controlled substances can shed light on issues related to the kidney, liver, and similar concerns.

With continued reference to FIG. 1A, contextual data may be used to provide understanding that the user or entity associated with the data is a critical part of contextual information. This may encompass user profiles, demographics, preferences, historical interactions, and behavioral patterns. In some cases, contextual data may be specific to a user chosen profession. For example, if the user has a profession that requires them to sit at a desk (i.e. Secretary, Lawyer, Financial professional, and the like.) processor 104 may infer that the user may live a more sedimentary life style as compared to a user with a non-sedimentary job (i.e. Construction Worker, Day Laborer, Professional Athlete, and the like.). When extracting the contextual data processor 104 may be configured to place the user dataset through preprocessing steps to clean, transform, and organize the data for further analysis. This could include handling missing values, standardizing formats, and converting unstructured data (e.g., text) into structured representations. In some embodiments, processor may generate contextual data as function of the metadata associated with user profile 108.

With continued reference to FIG. 1A, the processor may identify and segregate attributes the user profile 108 that contribute to the contextual understanding of the data. For instance, it could identify temporal attributes (timestamps), spatial attributes (location data), and other user-specific contextual attributes. Processor 104 may then engage in feature engineering, where it transforms the identified attributes into features suitable for analysis. This could involve creating new features, aggregating data, or deriving statistics to capture the context effectively. Depending on the application, processor 104 may integrate external contextual data sources (e.g., user profiles, device information) to enrich the contextual understanding. This could involve querying APIs, seeding web crawlers, accessing external databases, and the like. Utilizing the extracted metadata and engineered features, the processor may perform various analyses, such as statistical analysis, machine learning modeling, or data mining, to derive insights and predictions based on the context. The processor 104 combines the insights obtained from the analysis with the identified contextual attributes and metadata to generate contextual data. This could involve creating structured representations that encapsulate both the original data and the derived insights in a way that is understandable and useful.

With continued reference to FIG. 1A, processor 104 is configured to receive a user query 120 from a user. As used in the current disclosure, a "user query" is defined as a request or question posed by a user seeking information, assistance, or clarification on a specific topic or issue. The inquiry may be formulated using words, phrases, or specific medical terms that clearly articulate the user's needs or concerns. The user query 120 may be delivered to processor 104 through various mediums, including but not limited to, a chatbot, text fields, voice commands, email inputs, and direct user interface interactions. A chatbot may be a chatbot as described herein below in FIG. 7. A user query 120 may be submitted in formats such as text, images, audio, video, or a combination thereof. In an embodiment, the user query 120 may be intricately related to one or more aspects of the user profile 108 or the medical tests 112, potentially requiring detailed examination and responsive data retrieval from these components as discussed in greater detail below. For example, a user query 120 may include inquiries related to interpretations of medical test results such as echocardiograms or electrocardiograms from the user profile 108. User queries 120 may be related to the generation of a medical report, discussed in greater detail herein below, related to one or more aspects of the user profile or medical tests 112. Non-limiting examples of user queries 120 may include requests such as "Construct the echocardiography report by analyzing the given ECG;" "Interpret the stress echo outcomes based on this resting ECG;" "Generate the ECG report for this particular ECG recording;" "Analyze this specific ECG and present findings related to the left ventricle;" "Given the patients history of smoking, what is the likelihood that the patient has pulmonary hypertension based of their ECG?;" "Ask about past medical history, for instance, 'Have you ever been diagnosed with cancer?';" "Examine this ECG and generate findings specifically related to the mitral valve;" "Produce a detailed report focusing on the pericardium/epicardium from this specific electrocardiogram;" "Analyzing this ECG, is long QT a likely condition for the patient?" "Can right bundle branch block be identified in the patient through this ECG?" "Does this ECG show left axis deviation?" and other related queries that require the processor to engage with complex medical data analysis.

With continued reference to FIG. 1A, processor 104 generates testing data 124 as a function of the plurality of medical tests 112 using an encoder 128. As defined in the current disclosure, "testing data" refers to the digital representation of the medical tests 112. This may encapsulate various diagnostic outcomes transformed into a structured digital format. Processor 104 employs encoder 128 to convert the raw data from medical tests-which might include imaging scans, electrocardiograms, lab test results, and other diagnostic outputs-into standardized digital forms that can be easily processed, analyzed, stored, and communicated. Generation of testing data 124 may include transcription of numerical values and categorical results and the digitization of complex images and waveforms from tests such as ECG, EKG, MRIs, CT scans, Echocardiograms and the like. The resulting testing data 124 may be comprised of highly detailed and accurately rendered digital files that retain all critical medical and diagnostic information in a format suitable for integration into electronic health records (EHRs), for use in medical analysis software, or for transmission to other medical professionals for further evaluation. The integrity and precision of testing data 124 are crucial, as they directly influence the reliability of subsequent analyses and medical decisions based on this information.

With continued reference to FIG. 1A, medical tests 112 that include ECG signals may be converted to testing data 124. Testing data 124 generated by encoder 128 may include detailed digital representations of both types of cardiovascular diagnostics. For ECG, the testing data 124 may include digitized waveforms representing the electrical activity of the heart, capturing elements such as the P-wave, QRS complex, T-wave, and U-wave, along with calculated intervals and rates that provide insights into cardiac rhythm and function. Each waveform may be encoded with precision, ensuring that details like amplitude and timing are accurately represented in the digital output.

With continued reference to FIG. 1A, medical tests 112 that include the results of an echocardiogram may be converted to testing data 124. The testing data 124 that is representative of the echocardiogram may include high-resolution digital images and possibly video sequences that illustrates the heart's structural and functional characteristics during its operational cycle. This may include images of the heart chambers, valves, and walls, as well as Doppler ultrasound data that measures blood flow and heart muscle movements. The echocardiogram data may be enhanced with annotations that describe measurements like chamber dimensions, wall thickness, and ejection fraction, providing a comprehensive view of cardiac anatomy and performance.

With continued reference to FIG. 1A, the testing data 124 may include several layers of detail and utility that extend beyond basic digital conversion. This testing data 124 may include a wide array of digital outputs, each formatted according to specific data standards that ensure compatibility and interoperability across different healthcare information systems. For instance, testing data 124 may include structured data sets that encapsulate discrete values such as blood test measurements, blood pressure readings, or heart rate statistics, or other all coded in universally recognized medical coding systems like LOINC or SNOMED CT. In some embodiments, testing data 124 may include metadata, which may provide context about the medical tests 112 such as the time of the test, the conditions under which it was performed, and specifics about the test equipment used (e.g., model of the MRI or ECG machine). This metadata may be crucial for ensuring that the data can be accurately interpreted and utilized by healthcare providers. In addition to numerical and textual data, testing data 124 may also include complex graphical representations such as the digital images from scans, echocardiograms, or radiographs, converted into formats like DICOM (Digital Imaging and Communications in Medicine), which supports detailed medical imaging data and associated annotations.

With continued reference to FIGS. 1A-D, testing data 124 may be generated using an encoder 128. As used in the current disclosure, an "encoder" is a device or software component that transforms raw data into a standardized digital format. Encoder 128 is specifically tasked with converting the diverse outputs from medical tests 112, which may include analog signals, visual images, documents, and raw textual data, into cohesive, structured digital files that can be further processed, stored, or transmitted within the healthcare information systems. The functionality of encoder 128 encompasses several key processes: it digitizes analog data, such as the electrical activity recorded during an electrocardiogram or the acoustic signals in an echocardiogram, turning these into digital waveforms. It also converts visual data from medical imaging tests, such as X-rays, MRIs, or ultrasounds, into digital images in formats suitable for medical use, such as DICOM. Additionally, encoder 128 applies data compression techniques to reduce the file size of the digital outputs, facilitating more efficient storage and faster transmission while maintaining the integrity of the data. In some cases, encoder 128 may ensure that the converted data adheres to relevant data standards and protocols, such as HL7 or FHIR for health information exchanges, ensuring that the testing data 124 is compatible across different electronic health record (EHR) systems and can be accurately interpreted and utilized by medical professionals and algorithms alike. In essence, encoder 128 acts as a bridge between the physical data collection processes and the digital healthcare infrastructure, enabling a seamless flow of high-fidelity, actionable medical data.

With continued reference to FIGS. 1A-D, encoder 128 may convert the outputs from medical tests 112 into structured testing data 124. This may involve a series of steps that ensure accurate digital representation, compatibility, and utility of the testing data in medical and healthcare settings. The encoder 128 may receive raw data from various medical tests 112, which can include a depiction of analog signals or the analog signal themselves from devices like electrocardiograms and echocardiograms, visual data from imaging tests such as MRIs, CT scans, and X-rays, as well as textual and numerical data from laboratory tests. For medical tests 112 that are represented as analog signals, encoder 128 may include an ADC functionality to convert these signals into digital form. This conversion may be useful for creating a precise digital representation of the continuous analog data, which often captures vital physiological functions such as heart rhythm, electrical activity of the heart, or brain activity. In some embodiments, encoder 128 may receive visual data from imaging based medical tests 112. Encoder 128 may convert this visual data into digital images. This step may involve resolution adjustment, contrast enhancement, and formatting images into standardized digital formats like DICOM, which is specifically designed to handle, store, and transmit medical imaging information along with associated metadata. In an embodiment, to ensure the digital data of the testing data can be easily accessed and understood across various healthcare systems, encoder 128 may normalize and/or standardize the data according to medical data standards such as HL7, FHIR, and LOINC. This may include coding laboratory results, diagnostic codes, and other medical information in a consistent manner. Encoder 128 may also apply data compression techniques to reduce the size of the digital files, making them easier to store and quicker to transmit without losing critical information. Additionally, encryption may be applied to ensure data security and privacy, safeguarding patient information during storage and transmission. Throughout the encoding process, quality assurance mechanisms may be implemented to check the accuracy and integrity of the testing data 124. This includes validating the digital data against expected patterns and known standards to ensure no vital information is lost or misrepresented during the conversion process.

With continued reference to FIGS. 1A-D, the encoder 128 can also be conceptualized as an encoder machine learning model designed to transform raw medical data into structured digital formats. This approach may leverage advanced algorithms and neural network architectures to enhance the accuracy, efficiency, and functionality of the encoding process. Encoder machine-learning model may be consistent with the machine-learning model described below in FIG. 2. Inputs to the encoder machine-learning model may include medical tests 112, user profile 108, contextual data, EHR 116, examples of testing data 124, and the like. Outputs to the encoder machine-learning model may include testing data 124 tailored to the medical tests 112. As a machine learning model, encoder 128 may function by learning from vast datasets of medical information, including prior test results, imaging data, and clinical outcomes. The model may be trained using supervised learning techniques, where it is provided with examples of raw input data (e.g., analog signals from ECGs, raw images from echocardiograms) alongside the desired output format (e.g., digital waveforms, processed and annotated images). In an embodiment, the encoder may be pretrained using self-supervised learning techniques by leveraging contrasting modalities, such as ECGs and unstructured text from electronic health records (EHRs). For example, the model may generate correlations between the raw analog signals from ECGs with the clinical notes and observations found in unstructured text. This dual-modality training allows the encoder to understand the relationships between the physiological data and the contextual medical information, enhancing its ability to accurately transform raw inputs into structured, clinically relevant outputs. Through iterative training processes, the model may learn to recognize patterns, nuances, and clinically relevant features within the data, enabling it to perform complex conversions that maintain both the medical integrity and the detailed nuances of the original tests. Encoder training data may include a plurality of data entries containing a plurality of inputs that are correlated to a plurality of outputs for training a processor by a machine-learning process. In an embodiment, encoder training data may include a plurality of medical tests 112 correlated to examples of testing data 124. Encoder training data may be received from a database. Encoder training data may contain information about medical tests 112, user profile 108, contextual data, EHR 116, examples of testing data 124, and the like. In an embodiment, encoder training data may be iteratively updated as a function of the input and output results of past encoder machine-learning model or any other machine-learning model mentioned throughout this disclosure. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model, and the like. different settings without the need for reconfiguration or retraining.

With continued reference to FIGS. 1A-D, the encoder 128 or any other machine learning model mentioned herein may be frozen. As used in the current disclosure, "freezing" a model refers to a specific process in which the parameters (weights and biases) of the model are set to be non-trainable after it has been adequately trained. This means that these parameters are no longer updated in response to further training data or during additional training sessions. In practice, freezing a machine learning model may involve setting its trainable attribute to false, effectively locking down its state. This action is typically done in the framework used for developing the model, such as TensorFlow or PyTorch, where specific commands or settings are applied to freeze the model layers. Once frozen, the encoder can still perform its function of transforming input data into a structured, standardized output but without any modification to its internal state. This is particularly important in regulatory environments, like healthcare, where changes to software behaviors can necessitate revalidation or recertification. Freezing may be employed once the model has achieved a desired level of accuracy and generalization on the training and validation datasets. Freezing the model stabilizes its behavior, making it more predictable when deployed in production environments. This is crucial for medical applications where consistent and reliable performance is necessary for clinical decision-making. Once frozen, the model may not require the computational resources associated with ongoing training, such as gradient calculations and weight updates, which can be resource-intensive. This efficiency is particularly valuable in operational environments where computational resources may be limited or where real-time performance is critical. In an embodiment, Freezing the model may help prevent overfitting, where a model becomes too closely fitted to the training data, and thus performs poorly on new, unseen data. By stopping further training, the model maintains its ability to generalize from the examples it has learned during the training phase. Frozen models may be easier to integrate with existing healthcare systems as their outputs remain constant once integrated. This stability facilitates scalability, as the same model can be deployed across.

With continued reference to FIGS. 1A-D, processor 104 is configured to generate textual data 132 that is representative of the testing data 124. As used in the current disclosure, "textual data" is information that is in the form of text. Textual data 132 may be a textual representation of the testing data 124. Textual data 132 may represent information that is originally captured in visual formats such as ECG, ECHO, MRI, X-ray images, and the like. Textual data 132 may be the descriptive representation of these images, articulating in words what the images depict about anatomical structures, physiological functions, or pathological findings. This conversion from visual to textual format is particularly beneficial for accessibility, documentation, and detailed analysis. In an embodiment, Textual data 132 that is representative of an ECG signal might describe the waveform characteristics, such as the heights of the P, Q, R, S, and T waves, their durations, and the intervals between them. It may also interpret these characteristics, noting any deviations from normal patterns that could indicate cardiac issues such as arrhythmias, ischemia, or hypertrophy. In an additional embodiment, textual data 132 that is representative of an ECHO could detail measurements of heart chamber sizes, wall thicknesses, and the motion of valves during the cardiac cycle. It could also describe the ejection fraction, which is a measurement of the percentage of blood leaving the heart each time it contracts and provide an interpretation regarding valve functions or evidence of fluid around the heart. In a third embodiment, the textual data 132 that is representative of a medical image may describe the observed anatomical structures, highlighting any abnormalities such as tumors, fractures, or signs of disease like inflammation or degenerative changes. This description might include the size, shape, and location of these findings within the body.

With continued reference to FIGS. 1A-D, textual data 132 may be generated through the use of algorithms that are used to analyze the testing data 124 to identify key features and abnormalities. This process often involves the use of machine learning models trained to detect and interpret specific patterns in medical images. This may be done using natural language generation (NLG) techniques, which can convert the structured data extracted from the images into comprehensive, human-readable text. In some cases, the textual data 132 may be standardized using medical terminology to ensure consistency and understandability across different healthcare providers and systems. This standardization also includes formatting the text to adhere to medical reporting standards, which may involve the use of specific templates or styles.

With continued reference to FIGS. 1A-D, processor 104 is configured to generate textual data 132 that is representative of the testing data 124 using a querying transformer model (q-former) 136. As defined in the current disclosure, the "querying transformer model" is a machine learning framework specifically designed to process, understand, and generate textual data based on testing data. This may include the diverse array of medical tests 112 and the testing data 124 derived from them. The querying transformer model 136 may utilize transformer architecture 140. As used in the current disclosure, "transformer architecture" is a type of deep learning model that relies on mechanisms called attention mechanisms. Attention mechanisms 144 may enable the model to weigh the importance of different words or features in the input data, focusing more on relevant parts to generate accurate outputs. This architecture is particularly adept at handling sequences of data, making it ideal for applications that involve natural language processing (NLP).

With continued reference to FIGS. 1A-D, Querying transformer model 136 may be consistent with the machine-learning model described below in FIG. 2. Inputs to the querying transformer model 136 may include user profile 108, testing data 124, medical tests 112, examples of textual data 132, and the like. Outputs to the querying transformer model 136 may include textual data 132 tailored to the testing data 124. transformer training data may include a plurality of data entries containing a plurality of inputs that are correlated to a plurality of outputs for training a processor by a machine-learning process. In an embodiment, transformer training data may include a plurality of testing data 124 correlated to examples of textual data 132. transformer training data may be received from a database. transformer training data may contain information about user profile 108, testing data 124, medical tests 112, examples of textual data 132, and the like. In an embodiment, transformer training data may be iteratively updated as a function of the input and output results of past querying transformer model 136 or any other machine-learning model mentioned throughout this disclosure.

With continued reference to FIGS. 1A-D, the Q-former 136 may include an attention mechanism 144. An attention mechanism 144 may allow the model to focus on different parts of the input sequence when predicting each part of the output sequence. The querying transformer model 136 may not process data in order. Instead, they compute outputs based on a weighted combination of all input elements, which may be determined by the attention mechanism 144. An attention mechanism 144 may include a self-attention mechanism. This may be a mechanism that allows each position in the decoder to attend over all positions in the input sequence to better encode the same sequence. This helps the model to capture internal dependencies within the input data. An attention mechanism 144 may include a multi-head attention mechanism. The Q-former 136 may extend the self-attention mechanism by having multiple 'heads' of attention, allowing the model to jointly attend to information from different representation subspaces at different positions. This facilitates the model in capturing a richer diversity of relationships in the data.

With continued reference to FIGS. 1A-D, the querying transformer model 136 may be structured into two transformer-based encoders, one for ECG data and one for text data. Each encoder may include a series of identical layers, with each layer containing two sub-layers: a multi-head self-attention mechanism and a position-wise fully connected feed-forward network. Both sub-layers may be surrounded by residual connections followed by layer normalization. Each layer in the encoders may include a feed-forward neural network, applying the same linear transformations across all positions, separated by ReLU activations. This architecture's ability to process all input tokens simultaneously may enable faster training compared to recurrent models. It may also consumes less memory, making it suitable for processing longer sequences. FIGS. 1A-D.

With continued reference to FIGS. 1A-D, a multi-head attention mechanism may allow the model to attend to information from different representation subspaces at various positions, thus enriching the model's contextual understanding. The querying transformer model 136 may not inherently process data in sequence, they employ positional encodings to add information about the position of tokens within the sequence. This may be crucial for maintaining the sequence's order, which is vital for tasks that depend on understanding the relationships and contexts within sentences.

With continued reference to FIGS. 1A-D, the querying transformer model 136 may be trained using a multi-stage training process. In the first training stage, the model may be trained to handle and integrate testing data 124 and its accompanying caption, derived from descriptions of the medical tests 112. This stage may be done to ensure that the model learns to correctly associate specific testing data 124 patterns with their corresponding textual interpretations or descriptions. The model may take as input pairs labeled as testing data 124 and the caption which are derived from previous steps in the pipeline. These pairs may be referred to as <E, T> pairs throughout the disclosure. Where the E is represented by the testing data 124, wherein as the T may be representative of descriptive caption of the testing data 124. In an embodiment, T may also be an example of textual data 132. These pairs may consist of testing data 124 and their corresponding textual captions which have been prepared to train the model. In an embodiment, for each pair, the model generates embeddings where both the testing data 124 and the caption are transformed into the uniform vector space.

As used in the current disclosure, an "embedding" is a representation of data where elements of the data (such as words, phrases, images, or symbols) are mapped to vectors of real numbers in a lower-dimensional space relative to the high-dimensional space of the input data. This vector representation captures some semantics of the input by placing semantically similar inputs closer together in the embedding space. In an embodiment, generating embeddings may include transforming the embeddings into a uniform vector space. As used in the current disclosure, a "unified vector space" is a conceptual and computational framework where different types of data-such as text, images, and sounds—are transformed into vectors within the same multidimensional space. This transformation facilitates the comparison, association, and combination of various data types by representing them as points or vectors in a shared space with consistent dimensions and scales. This step may bring two different types of data—images (testing data 124) and text—into a unified representation that can be further processed. This embedding may be distinct from the token space used in large language models (LLMs), focusing instead on creating a foundational representation that correlates the visual and textual data effectively.

With continued reference to FIGS. 1A-D, computing device may optimize these embeddings by optimizing one or more loss functions. In an embodiment, a loss function may include image-text contrastive loss. This loss function may aim to minimize the distance between the correct <E, T> pairs in the vector space while maximizing the distance between mismatched pairs (where T does not accurately describe E). By doing this, the model learns to closely associate relevant testing data 124 with their correct descriptions while distinguishing them from irrelevant or incorrect descriptions. In another embodiment, a loss function may include Image-Text Matching Loss. Image-Text Matching Loss may be a binary classification loss where the model predicts whether a given T correctly corresponds to E. The output is binary (1 for correct matches, 0 for incorrect matches), helping the model to refine its accuracy in matching textual descriptions directly to the corresponding testing data 124. This loss reinforces the model's ability to discern and validate the appropriateness of text fragments for given testing data 124 images. In a third embodiment, a loss function may include Image-Text Generative (GPT) Loss. This loss function may leverage a generative approach, this loss function may encourage the model to generate text (T) that can be expected from the testing data 124 (E). This method not only focuses on matching but also on generating coherent, relevant textual output based on the input testing data 124. It integrates the generative capabilities of models like GPT to enhance the textual output's relevance and accuracy.

With continued reference to FIGS. 1A-D, the collective use of these three losses during the training phase may allow the Q-former to effectively learn the complex task of correlating testing data 124 with its appropriate textual representation. The multi-faceted approach ensures that the model is not only good at identifying correct matches but also at generating plausible textual descriptions when presented with new, unseen testing data 124. This training methodology is designed to equip the Q-former with robust capabilities for practical applications, such as automated medical diagnostics and intelligent data annotation in healthcare systems.

With continued reference to FIGS. 1A-D, in the second stage of training the Q-former 136, the focus may shift to integrating and fine-tuning the interaction between the Q-former 136 and a report large Language Model (LLM), discussed in greater detail herein below. This stage may be designed to ensure that the embeddings produced by the Q-former 136 align closely with the token space of the report LLM 148, which is critical for effective end-to-end model performance. In an embodiment, the second set of training may employ a second set of data pairs. The training utilizes curated data pairs labeled as <I, R>, where "I" represents a user query 120, and "R" corresponds to a medical report 152, which will be discussed in greater detail herein below. Each pair from the Q-former 136, <E, I> (where E represents the testing data 124 and/or textual data 132 processed in the first stage and I is the user query 120), is fed into the report LLM 148. This combined input prompts the LLM to generate a medical report 152. This step ensures that both components of the data, derived from the testing data 124 and/or textual data 132 (E) and user query 120 (I), are being used to inform the response generation by the report LLM 148.

With continued reference to FIGS. 1A-D, during the response generation process by the report LLM 148, any discrepancies between the predicted response (R) and the actual response in the training data trigger the back-propagation mechanism. This mechanism updates both the Q-former 136 and the report LLM 148 simultaneously. As used in the current disclosure, a "back-propagation mechanism" is a mechanism training machine learning models that optimizes the model by minimizing the error between the predicted outputs and the actual target values. It is employed after the forward pass, which involves feeding input through the neural network to produce an output. The output's deviation from the expected result is quantified using a loss function, which measures the prediction error. The essence of backpropagation is to adjust the model's internal parameters (weights and biases) in a way that reduces this loss. The process may begin by calculating the gradient of the loss function with respect to each parameter, essentially determining how much each parameter contributed to the error. This calculation relies on the chain rule of calculus and is performed from the output layer back toward the input layer-hence the term "back-propagation." These gradients are then used to make incremental adjustments to the parameters, typically via an optimization algorithm like stochastic gradient descent. The adjustments are intended to decrease the error, refining the model's predictions.

With continued reference to FIGS. 1A-D, in an embodiment involving both the Q-former 136 and the report LLM 148, back-propagation may be used to synchronize and optimize the joint training process. During training, both the Q-former 136 and the report LLM 148 receive input data. The Q-former 136 may process the initial inputs to generate embeddings that are then fed into the report LLM 148 alongside other contextual data. The LLM uses this comprehensive input to generate an output or response. Once the report LLM 148 produces its output, the predicted response is compared to the actual desired response, and the loss is calculated. This loss reflects the effectiveness of both the input embeddings provided by the Q-former and the output generation capabilities of the LLM. The calculated loss may then be used to determine the gradients for both the Q-former 136 and the report LLM 148. Back-propagation may ensure that these gradients indicate how each part of both models should change to reduce the loss. This may mean adjusting the Q-former's 136 embedding mechanisms as well as the report LLM 148 response generation parameters. These gradients may be applied simultaneously to update the parameters of both the Q-former 136 and the report LLM

148. The updates may be designed to improve the Q-former's 136 ability to produce more accurate and useful embeddings for the report LLM 148 and to enhance the LLM's capacity to generate more precise responses based on these embeddings.

With continued reference to FIGS. 1A-D, encoder that transforms testing data into a testing data representation, Q-former 136 that converts this representation into a "testing data-textual data" embedding space, and report LLM 148 that generates the output medical report by conditioning on the input query/instruction and the Q-former output, are all involved in the learning process through back-propagation. Additionally, a projection head, a multilayer perceptron (MLP), is used to transform Q-former output representation into the LLM language embedding space, ensuring the embedding dimensions match the LLM vocabulary embedding dimensions. In an embodiment, the weights of the Q-former, projection network, report LLM 148, and optionally the encoder, may be optimized through instruction fine-tuning in stage I, using a causal language modeling approach, and alignment techniques such as direct preference optimization (DPO) in stage II. As a non-limiting example, instruction fine-tuning may involve the following steps: 1). User query/instruction embeddings (obtained from the embedding matrix of report LLM 148) and embeddings of medical testing data from the projection head may be concatenated together, and this combined embedding may serves as input to report LLM 148; and 2) report LLM 148 may predict the next tokens (medical report) step by step using cross-entropy loss over all vocabulary tokens as the cost function, and the weights of all the components involved in the computation graph, including the Q-former 136, projection head, report LLM 148 (via LoRA or full fine-tuning), and optionally the encoder, may be updated using an optimizer, such as an AdamW optimizer. Additionally, or alternatively, for DPO, the process is similar, but the direct preference optimization cost function may be used.

With continued reference to FIGS. 1A-D, In the second stage of training the Q-former 136, processor 104 may procure the adjustment of the Q-former's 136 weights and the embeddings for input E. The updates are specifically aimed at adjusting the output <E, I> such that it seamlessly aligns with the LLM's token space. In an embodiment, the output of the Q-former 136 may be a textual data 132 that is representative of the testing data and a user query 120. Placing the testing data 124 into a textual format may allow the testing data 124 to fit into the token space that is required for the report LLM 148. This alignment is essential for ensuring that the embeddings from the Q-former 136 can be effectively processed and utilized by the LLM without requiring translation or re-encoding. In an embodiment, the goal of the second training stage may be for the Q-former 136 to produce outputs that are not just compatible but are native to the report LLM 148 token space. Achieving this means that the Q-former's outputs can be directly fed into the LLM as part of its natural processing pipeline, facilitating smoother and more efficient interaction between the two models.

With continued reference to FIGS. 1A-D, once the q-former 136 has been through both training stages, the Q-former 136 should be fully integrated with the report LLM 148, with both models functioning as a cohesive unit. This integration may allow for a more dynamic and contextually aware system, capable of handling complex queries and generating accurate, relevant responses based on a deep understanding of both medical imagery and associated textual data. This enhanced capability is particularly valuable in applications requiring nuanced understanding and generation of medical content, where accuracy and contextual relevance are paramount.

With continued reference to FIGS. 1A-D, processor 104 may be configured to generate a medical report 152 as a function of the user query 120 and the textual data 132 using a report large language model (LLM) 148. As used in the current disclosure, a "medical report" is a document that consolidates findings, interpretations, and clinical recommendations based on the analysis of specific medical imaging and test results. This report may be tailored to include detailed assessments such as rest echo reports, stress echo reports, ECG reports, and findings related to specific cardiac structures like the left ventricle, mitral valve, pericardium/epicardium, as well as conditions such as right bundle branch block or left axis deviation. The generation of a medical report 152 may begin with the processing of medical tests, where each test—be it an echocardiogram, electrocardiogram, or other specialized imaging procedures—is first analyzed either by automated systems to extract crucial diagnostic information. The textual data 132 derived from these tests may encompass detailed descriptions of observed physiological features and any anomalies that might indicate pathology. For instance, an ECG report might detail the heart's electrical activity, noting any irregular rhythms or patterns that suggest specific heart conditions, while an echo report might evaluate the structure and function of the heart's chambers and valves, providing measurements like chamber sizes, wall thickness, and valve functionality. In responding to a specific user query 120, the medical report 152 may integrate relevant sections of these individual test analyses to construct a narrative that addresses the query. If a user asks about left ventricular function, the medical report 152 may collate data from echo tests that measure the left ventricle's dimensions, wall motion, and ejection fraction, presenting a cohesive analysis that evaluates the ventricle's performance. Similarly, for a query concerning the mitral valve, the report would detail the valve's morphology and motion, potentially noting any regurgitation or stenosis. In an embodiment, the report might include comparative analyses over time, especially if previous test results are available, providing insights into the progression or improvement of a condition. It may also suggest potential therapeutic interventions, preventive measures, and follow-up tests needed based on the findings. Each section of the report may be carefully formatted to ensure clarity and ease of understanding, often supplemented with images or graphs for visual reference.

With continued reference to FIGS. 1A-D, the medical report 152 may encompass various types of reports such as cardiac CT reports, cardiac MRI reports, stress echocardiography reports, and chest X-ray reports. Each report may be tailored to the specific input medical data, ensuring that the findings and interpretations are relevant and accurate. For instance, a cardiac CT report might detail coronary artery calcifications and stenosis, while a cardiac MRI report could provide insights into myocardial function and tissue characterization. A stress echocardiography report might focus on the heart's performance under stress conditions, evaluating ischemia or wall motion abnormalities. Similarly, a chest X-ray report might identify pulmonary or cardiac pathologies like effusions or cardiomegaly.

With continued reference to FIGS. 1A-D, a medical report 152 may be a document used to provide a detailed and systematic analysis of a patient's health status based on diagnostic tests and examinations. This medical report 152 may serve as a comprehensive record that compiles and interprets data from various medical tests, such as echocardiograms (both rest and stress), electrocardiograms, and other specialized imaging studies, to assess and diagnose conditions related to the heart and other organs. In a non-limiting example, a medical report 152 focusing on echocardiographic outcomes might detail measurements of heart chamber sizes, ventricular function, and valve performance, providing insights into potential abnormalities such as valve regurgitation or ventricular hypertrophy. A section of the medical report 152 might be dedicated to the left ventricle, describing its pumping efficiency, wall thickness, and any signs of dilation or compromised function, which are critical for diagnosing conditions like heart failure or cardiomyopathy. In a second non-limiting example, an ECG report included within the broader medical document may analyze the electrical activity of the heart, pinpointing issues such as arrhythmias, ischemia, or evidence of a previous myocardial infarction. Additional details might include interpretations of specific findings like right bundle branch block or left axis deviation, each described in terms of their clinical implications and potential underlying causes. In some embodiments, the report may also serve as a dynamic document that not only describes current findings but often compares them against previous results to track the progression of a disease or the impact of treatments. This longitudinal analysis is crucial for chronic conditions where management depends heavily on changes over time. In some cases, beyond diagnostic data, a medical report may provide recommendations for treatment plans, further testing, or lifestyle changes based on the compiled data and its interpretation. This might include specific medications, surgical interventions, or referrals to specialists. It also advises on follow-up schedules to monitor the condition effectively.

With continued reference to FIGS. 1A-D, the medical report 152 may include an electrocardiogram report. As defined in the current disclosure, an "ECG report" is a focused document that analyzes and interprets the electrical activity of the heart captured during an ECG test. An ECG report may be a component of the broader medical report 152 generated by processor 104 as a function of user query 120 and the textual data 132, utilizing the capabilities of a report large language model (LLM) 148. This report may include detailed assessments of the rhythm and electrical patterns of the heart, such as the heart rate, rhythm regularity, and the timing and amplitude of specific ECG components like the P wave, QRS complex, ST segment, and T wave. In the ECG report, specific findings may be systematically detailed, including the presence of any arrhythmias, signs of myocardial ischemia or infarction, and other conduction abnormalities like right bundle branch block or left axis deviation. Each of these findings is described in terms of its clinical implications, potential underlying causes, and its significance in the context of the patient's overall cardiovascular health. For example, a section of the ECG report might delve into the characteristics of the QRS complex, discussing any abnormalities found in its configuration and what they might indicate about the heart's conduction pathways and ventricular health. In an embodiment, based on the findings detailed in the ECG report, specific recommendations may be made. These might include further diagnostic testing such as echocardiography or stress testing, therapeutic interventions including pharmacological treatment or lifestyle modifications, and scheduling follow-up tests to closely monitor cardiac function. Each recommendation may be tailored to the individual patient's diagnostic results and overall health context, ensuring that the medical report 152 provides a comprehensive and actionable plan that addresses both current health concerns and preventive healthcare strategies.

With continued reference to FIGS. 1A-D, with continued reference to FIGS. 1A-D, the medical report 152 may include an echocardiogram report. As used in the current disclosure, an "echocardiogram report" is a document that analyzes the characteristics of the heart using ultrasound imaging. The echocardiogram report provides a comprehensive evaluation of various cardiac features, including the size and movement of the heart chambers, the condition and operation of the heart valves, and the overall cardiac performance. The echocardiogram report may include key measurements such as the dimensions of the heart chambers, wall thicknesses, and the motion of the heart valves are meticulously detailed. These measurements are crucial for assessing the heart's pumping efficiency and for diagnosing conditions such as dilated cardiomyopathy, hypertrophic cardiomyopathy, and valvular heart diseases. For example, the report might highlight any abnormalities in the left ventricle's size or function, which are indicative of potential heart failure or other cardiac conditions. It also assesses ventricular function by measuring parameters like the ejection fraction, which indicates how much blood the left ventricle pumps out with each contraction. In some embodiments, the echocardiogram report might include findings on valve performance, noting issues such as stenosis (narrowing of the valve) or regurgitation (leakage of the valve), which can significantly impact cardiac output and overall cardiovascular health. These valve assessments are complemented by Doppler studies, included within the echocardiogram report, which measure the flow of blood through the heart and across the valves, providing additional diagnostic information about the pressure and gradient changes within the heart chambers. The echocardiogram report may be crafted to address specific inquiries from the user query 120, such as questions regarding the mitral valve or the function of the left ventricle. It integrates the current findings with historical data, if available, to offer insights into the progression or improvement of the patient's cardiac condition. This longitudinal perspective is essential for managing chronic cardiac conditions, allowing clinicians to adjust treatments or recommend further diagnostic testing based on changes over time.

With continued reference to FIGS. 1A-D, processor 104 may generate a medical report 152 using a report machine-learning model. As used in the current disclosure, a "report machine-learning model" is a machine-learning model that is configured to generate medical report 152. Report machine-learning model may be consistent with the machine-learning model described below in FIG. 2. Inputs to the report machine-learning model may include testing data 124, medical tests 112, textual data 132, user queries 120, and the like. Outputs to the report machine-learning model may include medical report 152 tailored to the user query 120 and textual data 132. Report training data may include a plurality of data entries containing a plurality of inputs that are correlated to a plurality of outputs for training a processor by a machine-learning process. In an embodiment, report training data may include a plurality of user query 120 and textual data 132 correlated to examples of medical report 152. Report training data may be received from a database. Report training data may contain information about testing data 124, medical tests 112, textual data 132, user queries 120, examples of medical report 152, and the like. In an embodiment, report training data may be iteratively updated as a function of the input and output results of past report machine-learning model or any other machine-learning model mentioned throughout this disclosure.

Still referring to FIGS. 1A-D, report machine-learning model includes a large language model (LLM). A "large language model," as used herein, is a deep learning data structure that can recognize, summarize, translate, predict and/or generate text and other content based on knowledge gained from massive datasets. Large language models may be trained on large sets of data. Training sets may be drawn from diverse sets of data such as, as non-limiting examples, novels, blog posts, articles, emails, unstructured data, electronic records, and the like. In some embodiments, training sets may include a variety of subject matters, such as, as nonlimiting examples, medical report documents, electronic health records, medical reports, medical textbooks, documentation provided by a medical professional, diagnostic reports, newspaper articles, and the like. In some embodiments, training sets of an LLM may include information from one or more public or private databases. As a non-limiting example, training sets may include databases associated with an entity. In some embodiments, training sets may include portions of documents associated with the electronic records correlated to examples of outputs. In an embodiment, an LLM may include one or more architectures based on capability requirements of an LLM. Exemplary architectures may include, without limitation, GPT (Generative Pretrained Transformer), T5 (Text-To-Text Transfer Transformer), Llama-2 7B, Zephyr 7B, and the like. Architecture choice may depend on a needed capability such generative, contextual, or other specific capabilities.

With continued reference to FIGS. 1A-D, in some embodiments, an LLM 148 may be generally trained. As used in this disclosure, a "generally trained" LLM is an LLM that is trained on a general training set comprising a variety of subject matters, data sets, and fields. In some embodiments, an LLM 148 may be initially generally trained. Additionally, or alternatively, an LLM 148 may be specifically trained. As used in this disclosure, a "specifically trained" LLM is an LLM that is trained on a specific training set, wherein the specific training set includes data including specific correlations for the report LLM 148 to learn. As a non-limiting example, an LLM 148 may be generally trained on a general training set, then specifically trained on a specific training set. In an embodiment, specific training of an LLM 148 may be performed using a supervised machine learning process. In some embodiments, generally training an LLM 148 may be performed using an unsupervised machine learning process. As a non-limiting example, specific training set may include information from a database. As a non-limiting example, specific training set may include text related to the users such as user specific data for electronic records correlated to examples of outputs. In an embodiment, training one or more machine learning models may include setting the parameters of the one or more models (weights and biases) either randomly or using a pretrained model. Generally training one or more machine learning models on a large corpus of text data can provide a starting point for fine-tuning on a specific task. A model such as an LLM 148 may learn by adjusting its parameters during the training process to minimize a defined loss function, which measures the difference between predicted outputs and ground truth. Once a model has been generally trained, the model may then be specifically trained to fine-tune the pretrained model on task-specific data to adapt it to the target task. Fine-tuning may involve training a model with task-specific training data, adjusting the model's weights to optimize performance for the particular task. In some cases, this may include optimizing the model's performance by fine-tuning hyperparameters such as learning rate, batch size, and regularization. Hyperparameter tuning may help in achieving the best performance and convergence during training. In an embodiment, fine-tuning a pretrained model such as an LLM 148 may include fine-tuning the pretrained model using Low-Rank Adaptation (LoRA). As used in this disclosure, "Low-Rank Adaptation" is a training technique for large language models that modifies a subset of parameters in the model. Low-Rank Adaptation may be configured to make the training process more computationally efficient by avoiding a need to train an entire model from scratch. In an exemplary embodiment, a subset of parameters that are updated may include parameters that are associated with a specific task or domain.

With continued reference to FIGS. 1A-D, in some embodiments an LLM 148 may include and/or be produced using Generative Pretrained Transformer (GPT), GPT-2, GPT-3, GPT-4, and the like. GPT, GPT-2, GPT-3, GPT-3.5, and GPT-4 are products of Open AI Inc., of San Francisco, CA. An LLM 148 may include a text prediction-based algorithm configured to receive an article and apply a probability distribution to the words already typed in a sentence to work out the most likely word to come next in augmented articles. For example, if some words that have already been typed are "The patient likely has pulmonary," then it may be highly likely that the word "hypertension" will come next. An LLM 148 may output such predictions by ranking words by likelihood or a prompt parameter. For the example given above, an LLM 148 may score "you" as the most likely, "your" as the next most likely, "his" or "her" next, and the like. An LLM 148 may include an encoder component and a decoder component.

Still referring to FIGS. 1A-D, an LLM 148 may include a transformer architecture. In some embodiments, encoder component of an LLM 148 may include transformer architecture. A "transformer architecture," for the purposes of this disclosure is a neural network architecture that uses self-attention and positional encoding. Transformer architecture may be designed to process sequential input data, such as natural language, with applications towards tasks such as translation and text summarization. Transformer architecture may process the entire input all at once. "Positional encoding," for the purposes of this disclosure, refers to a data processing technique that encodes the location or position of an entity in a sequence. In some embodiments, each position in the sequence may be assigned a unique representation. In some embodiments, positional encoding may include mapping each position in the sequence to a position vector. In some embodiments, trigonometric functions, such as sine and cosine, may be used to determine the values in the position vector. In some embodiments, position vectors for a plurality of positions in a sequence may be assembled into a position matrix, wherein each row of position matrix may represent a position in the sequence.

With continued reference to FIGS. 1A-D, an LLM 148 and/or transformer architecture may include an attention mechanism. An "attention mechanism," as used herein, is a part of a neural architecture that enables a system to dynamically quantify the relevant features of the input data. In the case of natural language processing, input data may be a sequence of textual elements. It may be applied directly to the raw input or to its higher-level representation.

With continued reference to FIGS. 1A-D, attention mechanism may represent an improvement over a limitation of an encoder-decoder model. An encoder-decider model encodes an input sequence to one fixed length vector from which the output is decoded at each time step. This issue may be seen as a problem when decoding long sequences because it may make it difficult for the neural network to cope with long sentences, such as those that are longer than the sentences in the training corpus. Applying an attention mechanism, an LLM 148 may predict the next word by searching for a set of positions in a source sentence where the most relevant information is concentrated. An LLM 148 may then predict the next word based on context vectors associated with these source positions and all the previously generated target words, such as textual data of a dictionary correlated to a prompt in a training data set. A "context vector," as used herein, are fixed-length vector representations useful for document retrieval and word sense disambiguation.

Still referring to FIGS. 1A-D, attention mechanism may include, without limitation, generalized attention self-attention, multi-head attention, additive attention, global attention, and the like. In generalized attention, when a sequence of words or an image is fed to an LLM 148, it may verify each element of the input sequence and compare it against the output sequence. Each iteration may involve the mechanism's encoder capturing the input sequence and comparing it with each element of the decoder's sequence. From the comparison scores, the mechanism may then select the words or parts of the image that it needs to pay attention to. In self-attention, an LLM 148 may pick up particular parts at different positions in the input sequence and over time compute an initial composition of the output sequence. In multi-head attention, an LLM 148 may include a transformer model of an attention mechanism. Attention mechanisms, as described above, may provide context for any position in the input sequence. For example, if the input data is a natural language sentence, the transformer does not have to process one word at a time. In multi-head attention, computations by an LLM 148 may be repeated over several iterations, each computation may form parallel layers known as attention heads. Each separate head may independently pass the input sequence and corresponding output sequence element through a separate head. A final attention score may be produced by combining attention scores at each head so that every nuance of the input sequence is taken into consideration. In additive attention (Bahdanau attention mechanism), an LLM 148 may make use of attention alignment scores based on a number of factors. Alignment scores may be calculated at different points in a neural network, and/or at different stages represented by discrete neural networks. Source or input sequence words are correlated with target or output sequence words but not to an exact degree. This correlation may take into account all hidden states and the final alignment score is the summation of the matrix of alignment scores. In global attention (Luong mechanism), in situations where neural machine translations are required, an LLM 148 may either attend to all source words or predict the target sentence, thereby attending to a smaller subset of words.

With continued reference to FIGS. 1A-D, multi-headed attention in encoder may apply a specific attention mechanism called self-attention. Self-attention allows models such as an LLM 148 or components thereof to associate each word in the input, to other words. As a non-limiting example, an LLM 148 may learn to associate the word "you", with "how" and "are". It's also possible that an LLM 148 learns that words structured in this pattern are typically a question and to respond appropriately. In some embodiments, to achieve self-attention, input may be fed into three distinct fully connected neural network layers to create query, key, and value vectors. Query, key, and value vectors may be fed through a linear layer; then, the query and key vectors may be multiplied using dot product matrix multiplication in order to produce a score matrix. The score matrix may determine the amount of focus for a word should be put on other words (thus, each word may be a score that corresponds to other words in the time-step). The values in score matrix may be scaled down. As a non-limiting example, score matrix may be divided by the square root of the dimension of the query and key vectors. In some embodiments, the softmax of the scaled scores in score matrix may be taken. The output of this softmax function may be called the attention weights. Attention weights may be multiplied by your value vector to obtain an output vector. The output vector may then be fed through a final linear layer.

Still referencing FIGS. 1A-D, in order to use self-attention in a multi-headed attention computation, query, key, and value may be split into N vectors before applying self-attention. Each self-attention process may be called a "head." Each head may produce an output vector and each output vector from each head may be concatenated into a single vector. This single vector may then be fed through the final linear layer discussed above. In theory, each head can learn something different from the input, therefore giving the encoder model more representation power.

With continued reference to FIGS. 1A-D, encoder of transformer may include a residual connection. Residual connection may include adding the output from multi-headed attention to the positional input embedding. In some embodiments, the output from residual connection may go through a layer normalization. In some embodiments, the normalized residual output may be projected through a pointwise feed-forward network for further processing. The pointwise feed-forward network may include a couple of linear layers with a ReLU activation in between. The output may then be added to the input of the pointwise feed-forward network and further normalized.

Continuing to refer to FIGS. 1A-D, transformer architecture may include a decoder. Decoder may a multi-headed attention layer, a pointwise feed-forward layer, one or more residual connections, and layer normalization (particularly after each sub-layer), as discussed in more detail above. In some embodiments, decoder may include two multi-headed attention layers. In some embodiments, decoder may be autoregressive. For the purposes of this disclosure, "autoregressive" means that the decoder takes in a list of previous outputs as inputs along with encoder outputs containing attention information from the input.

With further reference to FIGS. 1A-D, in some embodiments, input to decoder may go through an embedding layer and positional encoding layer in order to obtain positional embeddings. Decoder may include a first multi-headed attention layer, wherein the first multi-headed attention layer may receive positional embeddings.

With continued reference to FIGS. 1A-D, first multi-headed attention layer may be configured to not condition to future tokens. As a non-limiting example, when computing attention scores on the word "am," decoder should not have access to the word "fine" in "I am fine," because that word is a future word that was generated after. The word "am" should only have access to itself and the words before it. In some embodiments, this may be accomplished by implementing a look-ahead mask. Look ahead mask is a matrix of the same dimensions as the scaled attention score matrix that is filled with "0s" and negative infinities. For example, the top right triangle portion of look-ahead mask may be filled with negative infinities. Look-ahead mask may be added to scaled attention score matrix to obtain a masked score matrix. Masked score matrix may include scaled attention scores in the lower-left triangle of the matrix and negative infinities in the upper-right triangle of the matrix. Then, when the softmax of this matrix is taken, the negative infinities will be zeroed out; this leaves zero attention scores for "future tokens".

Still referring to FIGS. 1A-D, second multi-headed attention layer may use encoder outputs as queries and keys and the outputs from the first multi-headed attention layer as values. This process matches the encoder's input to the decoder's input, allowing the decoder to decide which encoder input is relevant to put a focus on. The output from second multi-headed attention layer may be fed through a pointwise feedforward layer for further processing.

With continued reference to FIGS. 1A-D, the output of the pointwise feedforward layer may be fed through a final linear layer. This final linear layer may act as a classifier. This classifier may be as big as the number of classes that you have. For example, if you have 10,000 classes for 10,000 words, the output of that classifier will be of size 10,000. The output of this classifier may be fed into a softmax layer which may serve to produce probability scores between zero and one. The index may be taken of the highest probability score in order to determine a predicted word.

Still referring to FIGS. 1A-D, decoder may take this output and add it to the decoder inputs. Decoder may continue decoding until a token is predicted. Decoder may stop decoding once it predicts an end token.

Continuing to refer to FIGS. 1A-D, in some embodiment, decoder may be stacked N layers high, with each layer taking in inputs from the encoder and layers before it. Stacking layers may allow an LLM 148 to learn to extract and focus on different combinations of attention from its attention heads.

With continued reference to FIGS. 1A-D, a report LLM 148 may receive an input. Input may include a string of one or more characters. Inputs may additionally include unstructured data. For example, input may include one or more words, a sentence, a paragraph, a thought, a user query 120, and the like. A "query" for the purposes of the disclosure is a string of characters that poses a question. In some embodiments, input may be received from a user device. User device may be any computing device that is used by a user. As non-limiting examples, user device may include desktops, laptops, smartphones, tablets, and the like.

With continued reference to FIGS. 1A-D, a report LLM 148 may generate at least one annotation as an output. At least one annotation may be any annotation as described herein. In some embodiments, a report LLM 148 may include multiple sets of transformer architecture as described above. Output may include a textual output. A "textual output," for the purposes of this disclosure is an output comprising a string of one or more characters. Textual output may include, for example, a plurality of annotations for unstructured data. In some embodiments, textual output may include a phrase or sentence identifying the status of a user query. In some embodiments, textual output may include a sentence or plurality of sentences describing a response to a user query. As a non-limiting example, this may include restrictions, timing, advice, dangers, benefits, and the like.

With continued reference to FIGS. 1A-D, in initial stages of training report LLM 148, instruction fine-tuning may be employed to enhance the model's capability in understanding and generating medical report 152. As used in this disclosure, "instruction fine-tuning," also known as "supervised fine-tuning," is a re-training process involving usage of a labeled dataset. Labeled dataset may include, for example, and without limitation, a plurality of medical data and queries as input correlated to a plurality of medical reports as outputs. During the instruction fine-tuning phase, embeddings from user queries and medical testing data may be concatenated and fed into report LLM 148. Report LLM 148 may then predict subsequent tokens to form a coherent medical report using cross-entropy loss to evaluate the prediction accuracy. Following the initial fine-tuning, report LLM 148 may undergo reinforcement learning for further alignment and optimization as described below.

With continued reference to FIGS. 1A-D, generating the medical report 152 may include iteratively training the report LLM 148 using one or more reinforcement learning techniques. Training the report LLM 148 may include executing one or more reinforcement learning models configured to interact with an environment related to generating a medical report. As described herein, an "environment" is defined as a plurality of dynamic and/or static elements encountered by an "agent," also known as a "decision maker" (e.g., report LLM 148). In some cases, plurality of dynamic and/or static elements may include, without limitation, user query 120 and textual data 132. As a non-limiting example, agent may include a software program act as a "learner" in reinforcement learning, wherein the software program may interact with the environment by one or more actions and receive rewards or returns based on the one or more actions. In one or more embodiments, processor 104 may receive input data representative of at least one state of the environment. For example, and without limitation, input data may include user query 120 and textual data 132. One or more reinforcement learning models may be configured to process received input to determine at least an action based on a policy; for instance, and without limitation, at least an action may include generating a medical report 152 related to an echocardiogram or EKG that maximizes a reward function over time as described below, wherein the at least an action may be output to effect a change in the environment.

With continued reference to FIGS. 1A-D, in some embodiments, reinforcement learning models may be implemented as a function of Markov Decision Processes (MDPs) for sequential decision making in situations where outcomes are partly random and partly under the control of the agent. As a non-limiting example, MDP may be defined by a plurality of states(S) in the environment, a set of actions (A) the agent can take, at least one transition function T(s, a, s') i.e., a probability distribution that defines the likelihood of transitioning from a first state s to a second state s' given a specific action a, at least a reward function (R), and discount factor $\gamma$. In some cases, each of the one or more reinforcement learning models may configure the agent to learn one or more policy as described in further detail below. In some cases, training LLM 148 may involve solving MDPs using reinforcement learning algorithms as described herein by learning the optimal policy without knowing the MDP's transition and reward functions as priori. In some cases, each of the one or more reinforcement learning models may be configured to make a sequence of decisions wherein the outcome of each decision may influence future decision. Therefore, at least in part, each of the one or more reinforcement learning models may include a "Markov property" i.e., the future state dependents only on the current state and action, not on the sequence of events that preceded it.

With continued reference to FIGS. 1A-D, a "policy," for the purpose of this disclosure, is a strategy or a set of strategies that a corresponding reinforcement learning model employs to decide which action or a set of actions to take in a given state of the environment. As a non-limiting example, policy may include a function defining a probability distribution over a set of actions (a∈A) for each state (s∈S). In some cases, if agent at time t follows a policy π then the policy function π(a|s) may be the probability that the agent with taking action (a) at a particular time step (t). In an embodiment, a policy may be mathematically defined as π(a|s)= $\mathbb{P}$ [$A_t$=a|$S_t$=s]. In some cases, each of the one or more reinforcement learning models may include a different set of polices, for example, and without limitation, each reinforcement learning model may be implemented based on a different requirement or objectives of different components of the system or different operational scenarios. As a non-limiting example, a first model may focus on one or more short-term objectives such as immediate reward maximization, while a second model may prioritize one or more long-term objectives such as policy generalization or Long-term reward maximization. In some cases, policy may be formulated based on historical data, simulations, real-time feedback, and/or the like aiming to map observed environmental state to certain actions that achieve desired outcomes. In a non-limiting example, policy may dictate that when a predicated example of the medical report 152 is aligned with generated medical report 152 the report LLM 148 may be rewarded. Alternatively, when the predicted medical report 152 is not aligned the report LLM 148 may be punished.

With continued reference to FIGS. 1A-D, in some cases, reward function may quantitatively evaluate one or more outcomes of actions taken by the agent based on one or more predefined objectives. As a non-limiting example, rewards may be calculated as a function of corresponding actions and states (of the environment and/or the agent) in which the corresponding actions are taken. In an embodiment, reward function may include an immediate mapping from a state-action pair (and sometimes the resulting state) to a numerical value (i.e., reward) signifying an immediate benefit or cost of an action. As a non-limiting example, a reward function may be defined as R:S×A×S→$\mathbb{R}$, wherein S is the set of all states, A is the set of all actions, and $\mathbb{R}$ represents the real numbers indicating rewards. In some embodiments, reward function may depend only on the current state and action, not on the resulting state. In some case, a higher value may be assigned to generating predicted medical reports that will closely aligned with the output medical report 152. Conversely, the generation of medical reports that are misaligned within output medical report 152 may result in a lower value (i.e., a penalty). Exemplary factors may be utilized by processor 104 while implementing the reward function includes, without limitation, user query 120 and textual data 132. Reinforcement learning models may be configured to maximize the cumulative rewards or minimize the cumulative penalties over time to determine one or more desired actions that collectively optimize user query 120 and textual data 132 in training report LLM 148. Additionally, or alternatively, rewards may not be arbitrarily changed by the agent. As a non-limiting example, reward calculation as described herein may be considered to be part of the environment (since the agent cannot change the environment arbitrarily) event through the agent has the access on the definition of the reward function; therefore, at least in part, reward functions may be external to the agent.

With continued reference to FIGS. 1A-D, each of the one or more reinforcement learning models may employ a state-value function, also known as "V-Function," to determine a desired policy, wherein the state-value function is configured to estimate an expected return (i.e., total discounted future rewards) starting from a state s and following a particular policy it as described above. In some cases, state-value function may capture a long-term value of states S under that T. In an embodiment, the value of state s, when the agent is following policy π as described above, may be denoted by $V^\pi$(s) i.e., the expected return starting from s and following policy π for next states until reinforcement learning model reaches a terminal state (e.g., end state) as described in further detail below. In such the embodiment, training report LLM 148 may include one or more episodic tasks i.e., tasks having finite states. In other cases, training report LLM 148 may be continuous; for instance, and without limitation, training report LLM 148 may include tasks that have no terminal state. As a non-limiting example, state-value function may be defined as $$V^\pi(s) = \mathbb{E}\left[\sum_{k=0}^{\infty} \gamma^k R_{t+k+1} | S_t = s\right]$$

where γ is a discount factor and the $R_{t+k+1}$ are the rewards received at future times steps. Additionally, or alternatively, each of the one or more reinforcement learning models may employ a policy value function (also known as "Q-Function,") instead, wherein the policy value function estimates the expected return of taking an action a in state s and thereafter following policy π. In some cases, policy value function evaluates both the immediate action and the subsequent strategy (i.e., policy) according to following equation:

$$Q^\pi(s, a) = \mathbb{E}\left[\sum_{k=0}^{\infty} \gamma^k R_{t+k+1} | S_t = s, A_t = a\right].$$

With continued reference to FIGS. 1A-D, in some cases, discount factor may determine how much importance is to be given to an immediate reward and/or one or more future rewards. In some cases, discount factor γ may be configured to avoid infinity as a reward in case of training report LLM 148 being a continuous task. As a non-limiting example, discount factor γ may include a value between 0 and 1. In an embodiment, a value of 0 means that more importance is given to the immediate reward and a value of 1 means that more importance is given to future rewards. In some cases, a discount factor γ of 0 may never learn as it only considers immediate reward and a discount factor γ of 1 will go on for future rewards which may lead to infinity, therefore, at least in part, a desired discount factor γ may be a value between a range of 0.2~0.8. As a non-limiting example, a cumulative return $G_t$ at time t may be defined using discount factor γ as follows:

$$G_t = R_{t+1} + \gamma R_{t+2} + \gamma^2 R_{t+3} + \ldots + \gamma^k R_{t+k+1} = \sum_{k=0}^{\infty} \gamma^k R_{t+k+1}$$

Wherein a smaller discount factor γ may indicate a higher significance in early rewards as the rewards are getting significantly low at future time t+k+1, while a higher discount factor ɣ may means the corresponding reinforcement learning model is also interested in future rewards. Processor 104 may be configured to determine a discount factor ɣ depends on the task reinforcement learning models are trained for, for example, and without limitation, in training report LLM 148, if high importance is given to the immediate rewards such as immediate reward maximization, then the agent may be configured to learn to generate predicted medical reports that alight with the medical report 152 generated by LLM 148 no matter policy generalization. Further, in some cases, processor 104 may utilize Monte Carlo (MC) simulations to estimate value functions and policies as described herein based on agent experience e.g., sequence of states, actions, and rewards in uncertain environments. In one or more embodiments, training report LLM 148 using one or more reinforcement learning models may be based on averaging complete returns.

With continued reference to FIGS. 1A-D, in some embodiments, reinforcement learning models may be configured to update policy based on one or more feedbacks from the environment in response to the determined action, wherein the feedbacks may include one or more rewards or returns indicative of the effectiveness of the action in achieving objectives related to aligning the predicted medical report with the medical report generated by report LLM 148. As a non-limiting example, actions leading to the generation of an accurate medical report 152 would receive a positive reward or returns indicative of the effectiveness of the action in training report LLM 148. As another non-limiting example, actions that result in a point or score reduction may be met with a negative rewards or penalties. Processor 104 may be configured to iteratively adjust one or more policy based on cumulative feedback from the environment to optimize the performance of the system in training report LLM 148. One or more reinforcement learning model as described herein may incorporate techniques such as, without limitation, exploration versus exploration to occasionally choose less-optimal actions in the short term to explore the effects of different policy settings across different reinforcement learning models. In some cases, exploration may be balanced with exploitation of known policies that yield desirable outcomes e.g., generating a medical report 152.

With continued reference to FIG. 1, generating the medical report 152 may include iteratively training the report LLM 148 using one or more direct preference optimization techniques. Processor 104 may fine tune LLM 148 using one or more Direct Preference Optimization (DPO) techniques. As used in the current disclosure, "Direct Preference Optimization" is a technique for fine-tuning machine learning models, such as a Large Language Model (LLM), where the optimization is guided by explicit preferences provided by trainers. DPO may be represented as the solution to the objective function:

$$\mathcal{L}_{DPO}\left(\pi_\theta; \prod_{ref}\right) = -\mathbb{E}_{(x,y_w,y_l) \sim \mathcal{D}}\left[\log_\sigma\left[\beta \log \frac{\pi_\theta(\mathcal{Y}_w \mid X)}{\pi_{ref}(\mathcal{Y}_w \mid X)} - \beta \log \frac{\pi_\theta(\mathcal{Y}_l \mid X)}{\pi_{ref}(\mathcal{Y}_l \mid X)}\right]\right]$$

The objective function for DPO may aim to maximize the probability of chosen outcomes while minimizing the probability of rejected ones. The DPO may begin by presenting a pair of model outputs in response to a prompt: one that has been chosen (preferred by the trainers) and one that has been rejected. Both the "trained LLM" and a "frozen LLM" provide scores for these outputs. The trained LLM may be actively updated during training, while the frozen LLM remains static and serves as a reference point. The scores may then be used to compute a policy ratio, which compares the probabilities of the chosen and rejected responses under the current policy πθ to those under the reference policy π_ref. The parameter β controls the strength of preference; a higher value places more emphasis on following the chosen preferences. The loss function combines these scores and uses a logarithmic function to penalize the model when it assigns a higher score to rejected outputs over chosen outputs. By minimizing this loss function during training, the LLM learns to generate outputs that are more aligned with the preferences indicated by the trainers. The ultimate goal is to adjust the LLM's parameters to favor generating the chosen outputs while steering away from the rejected ones, effectively optimizing the model based on direct human feedback.

With continued reference to FIGS. 1A-D, Direct Preference Optimization (DPO) may be used to refine the training of a Large Language Model (LLM) by incorporating human judgments directly into the learning process. During the training process, for any given input x, the LLM generates a pair of outputs, $y_w$ (the one chosen by human trainers) and $y_l$ (the one rejected). These choices are based on which outputs more closely align with desired criteria such as correctness, fluency, or adherence to ethical guidelines. Both a trained version of the LLM, which is updated iteratively during training, and a frozen version, which remains constant and acts as a reference point, evaluate these outputs. Each version provides a score for how likely it is to produce each output given the same input x. In an embodiment, the core DPO may lie in the policy ratio within the logarithmic function, which calculates the ratio of the probabilities of producing the preferred and non-preferred outputs under the current model's policy $\pi_\theta$ versus a reference policy $\pi_{ref}$. This ratio indicates how much more or less likely the current policy is to generate the preferred responses compared to the reference policy. The parameter β may be crucial as it modulates the strength of the preference signal. By altering β, the model's sensitivity to the trainers' preferences is adjusted. A high β means that the model's training will heavily favor human-chosen outputs, reinforcing the model's inclination to replicate choices that humans prefer. The sigmoid function σ may be applied to the log odds computed from the policy ratio, transforming the values into a (0, 1) range, thus bounding the output probabilities. The loss function itself is designed to be minimized when the model prefers the chosen outputs $y_w$ and discounts the rejected ones $y_l$. This minimization process is the key to the model's learning, as it updates the model's parameters to align with the preferences expressed by the trainers. In essence, DPO may train the LLM to imitate human-like decision-making by making it more likely to produce outputs that human trainers find suitable. The loss function provides a clear gradient for the model to follow, with the human trainers' preferences serving as a guiding light. As a result, the model may become adept at generating outputs that not only are correct in a technical sense but also exhibit the nuanced understanding that reflects human values, cultural contexts, and subtleties of language use.

Still referring to FIGS. 1A-D, processor 104 may be configured to display medical report 152 on a display device 156. As used in the current disclosure, a "display device" is a device that is used to display content. A display device 156 may include a user interface. A "user interface," as used herein, is a means by which a user and a computer system interact; for example through the use of input devices and software. A user interface may include a graphical user interface (GUI), command line interface (CLI), menu-driven user interface, touch user interface, voice user interface (VUI), form-based user interface, any combination thereof, and the like. A user interface may include a smartphone, smart tablet, desktop, or laptop operated by the user. In an embodiment, the user interface may include a graphical user interface. A "graphical user interface (GUI)," as used herein, is a graphical form of user interface that allows users to interact with electronic devices. In some embodiments, GUI may include icons, menus, other visual indicators, or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pull-down menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface. For example, links to decentralized platforms as described in this disclosure may be incorporated using icons. Using an icon may be a fast way to open documents, run programs etc. because clicking on them yields instant access. Information contained in user interface may be directly influenced using graphical control elements such as widgets. A "widget," as used herein, is a user control element that allows a user to control and change the appearance of elements in the user interface. In this context a widget may refer to a generic GUI element such as a check box, button, or scroll bar to an instance of that element, or to a customized collection of such elements used for a specific function or application (such as a dialog box for users to customize their computer screen appearances). User interface controls may include software components that a user interacts with through direct manipulation to read or edit information displayed through user interface. Widgets may be used to display lists of related items, navigate the system using links, tabs, and manipulate data using check boxes, radio boxes, and the like.

Figure 2:
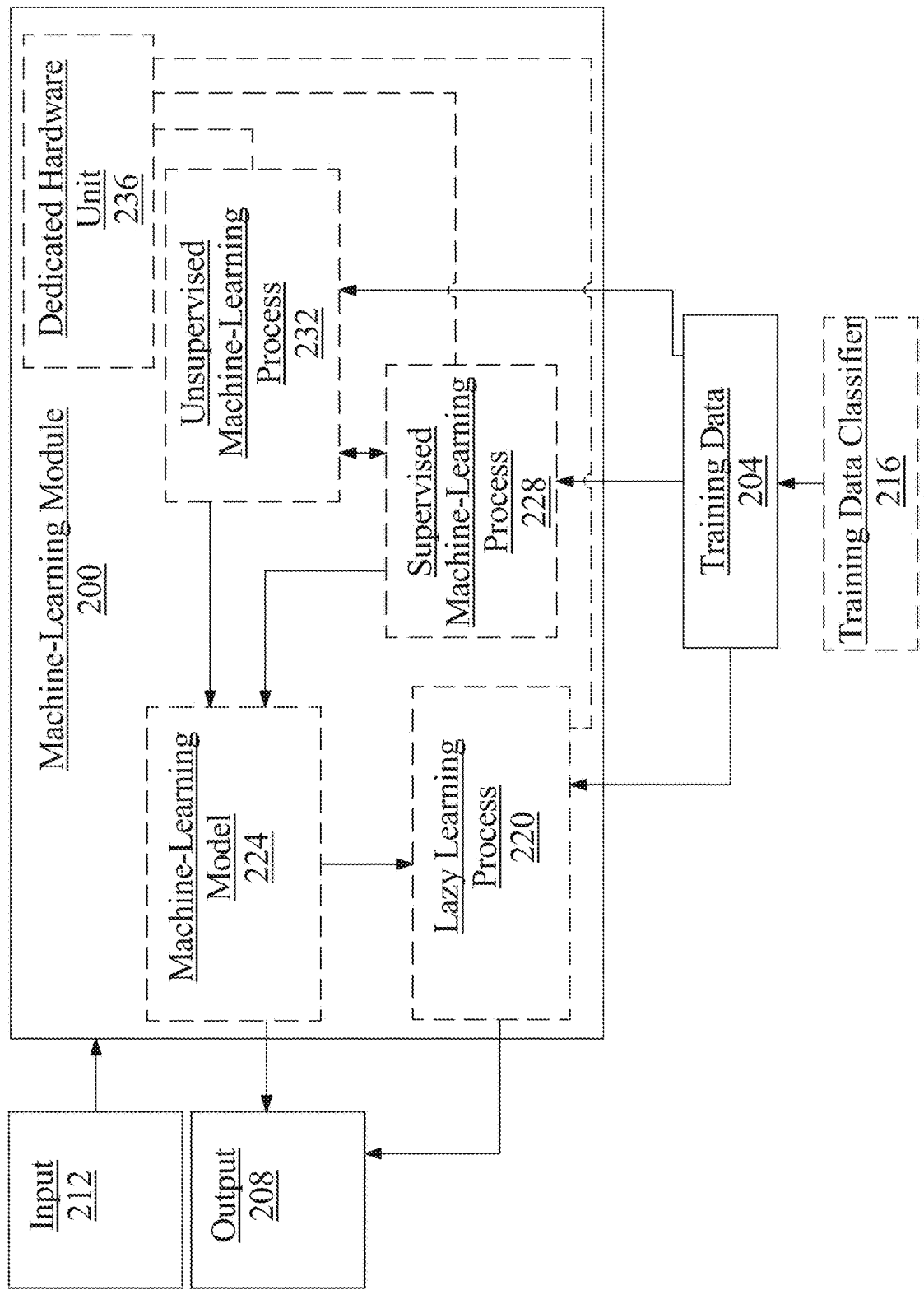
FIG. 2 is a block diagram of an exemplary machine-learning process.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm instantiated in hardware or software logic, data structures, and/or functions that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure. As a non-limiting illustrative example, inputs may include pairs of transformer training data comprises at least one example of testing data paired with at least one example of textual data that corresponds to the example of testing data as inputs correlated to textual data as outputs.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 200 may generate a classifier using a classification algorithm, defined as a processes whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to specific conditions and/or medical tests such as ECG, Echo, and the like.

With further reference to FIG. 2, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Still referring to FIG. 2, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value.

As a non-limiting example, and with further reference to FIG. 2, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity, and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 2, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels.

It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 2, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include [input examples] as described above as inputs, [output examples] as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

With further reference to FIG. 2, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 2, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 232 may not require a response variable; unsupervised processes 232 may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 2, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 2, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 2, retraining and/or additional training may be performed using any process for training described above, using any currently or previously deployed version of a machine-learning model and/or algorithm as a starting point. Training data for retraining may be collected, preconditioned, sorted, classified, sanitized, or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 2, one or more processes or algorithms described above may be performed by at least a dedicated hardware unit 236. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 236 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 236 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 236 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 3:
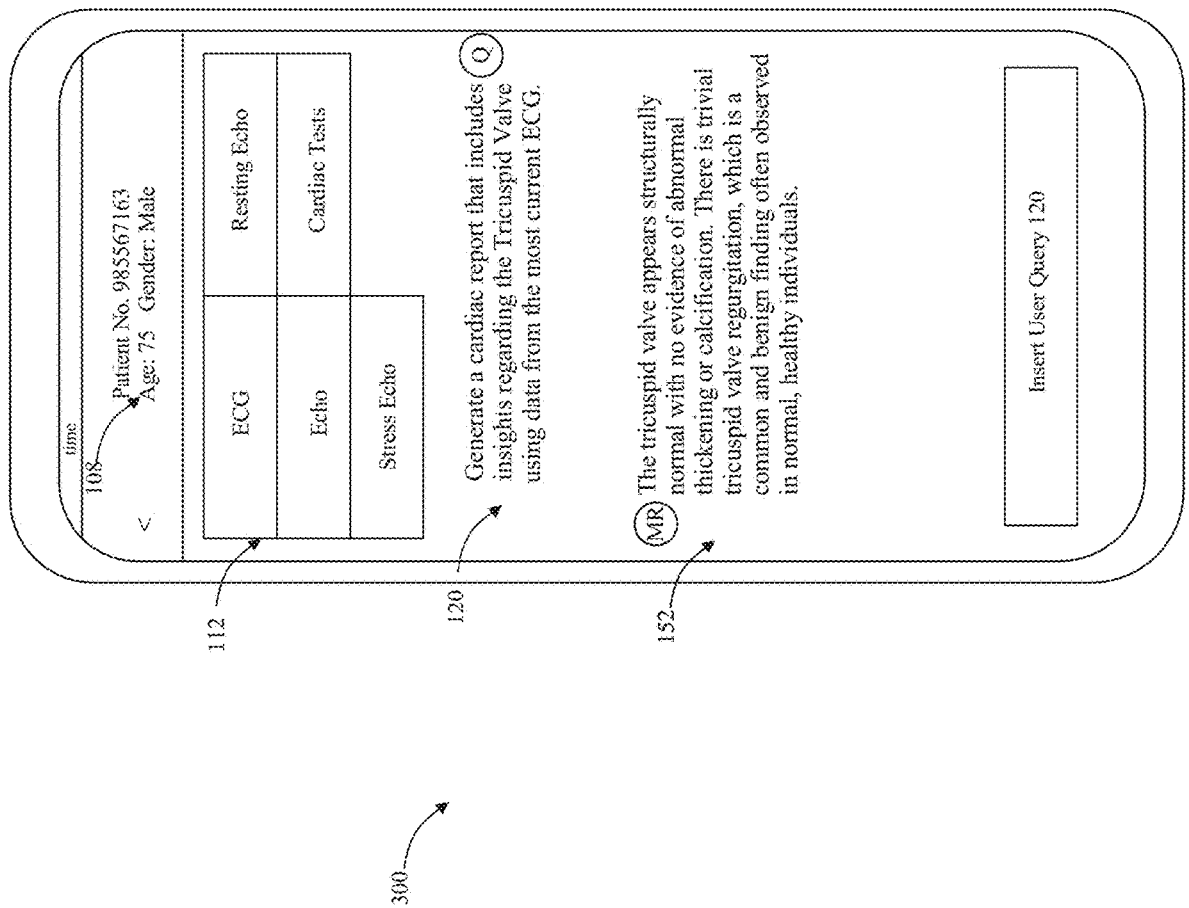
FIG. 3 is an illustration of an exemplary embodiment of a user interface.

Now referring to FIG. 3, an illustration of an exemplary embodiment of a user interface 300. User interface 300 displays an exemplary depiction of a medical report 152. Medical report 152 may provide details and explanation of a user's medical condition based on one or more medical tests 112 that have been performed on the user. In an embodiment, User interface 300 may include a chatbot that is configured to allow a user to submit a query 120. Once this query is submitted, the Encoder, Q-former, and LLM may work together to generate a medical report 152. For example, within the user interface 300, a user might input a query such as "Show the latest analysis on my heart function." In response, the system utilizes the Encoder to preprocess the input, the Q-former to correlate the query with relevant medical test data, and the LLM to synthesize and generate a medical report. The medical report 152 may then dynamically appear on the user interface, detailing the current state of the user's heart health based on recent tests, such as an echocardiogram or an ECG. The user interface 300 can also display graphical representations, including charts or graphs, which visualize trends over time in the user's cardiac functions or other health metrics. For instance, if the medical tests include serial echocardiograms, the user interface might display a graph charting changes in the ejection fraction or other parameters of heart function, offering the user a clear visual representation of their cardiac health progression or stability. Furthermore, user interface 300 may be designed to facilitate interaction via the chatbot, where users can ask follow-up questions or request further details. For example, a user might ask, "What does trivial tricuspid regurgitation mean?" The chatbot, leveraging the LLM's capabilities, can provide an instant explanation that contextualizes the finding within the user's specific medical context, explaining that this is a common finding that usually does not signify severe underlying heart disease. Additionally, a user may submit additional contextual data or processor 104 may request the additional contextual using the chatbot. In another embodiment, user interface 300 could allow for the customization of the displayed report. Users could select specific sections of the report to expand for more detailed information or to collapse sections they find less relevant. This customization feature makes the medical report 152 highly adaptable to individual user needs, enhancing user engagement and understanding. Additionally, the system behind user interface 300 may include functionality for sending notifications to users when new medical reports are generated or when follow-up tests are recommended based on the analysis provided by the LLM. This proactive feature aids in maintaining up-to-date health monitoring and ensuring continuous care management.

Figure 4:
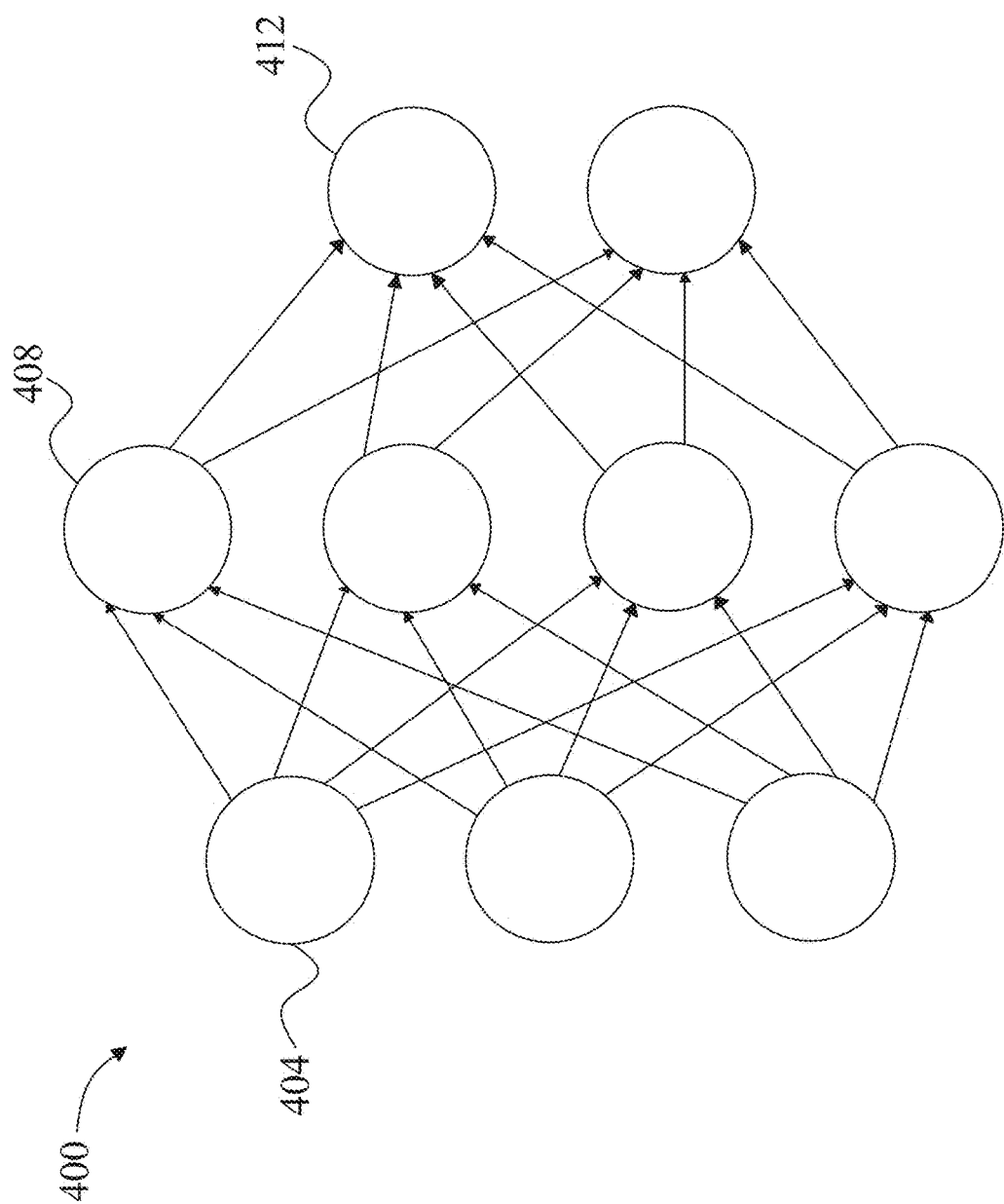
FIG. 4 is a diagram of an exemplary embodiment of a neural network.

Referring now to FIG. 4, an exemplary embodiment of neural network 400 is illustrated. A neural network 400, also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 5:
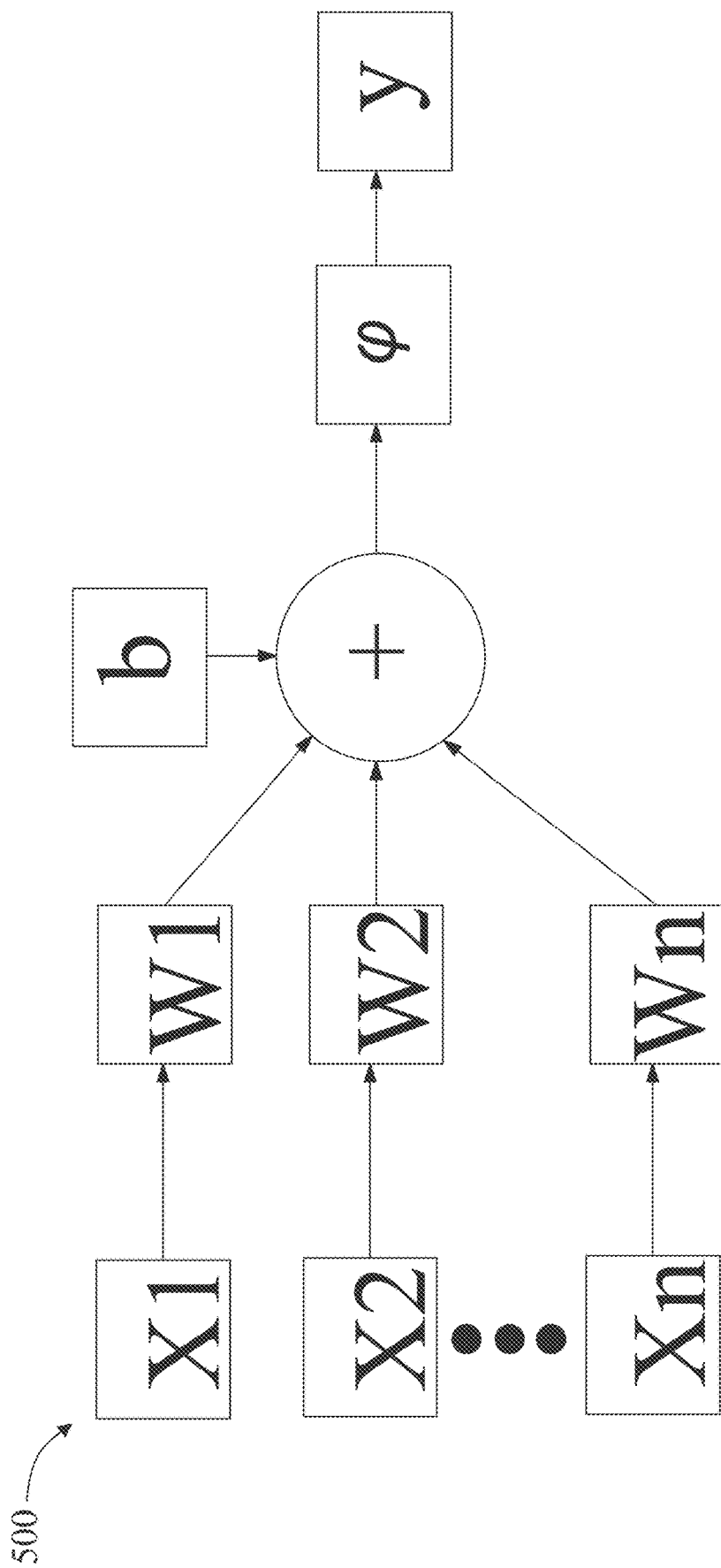
FIG. 5 is a diagram of an exemplary embodiment of a node of a neural network.

Referring now to FIG. 5, an exemplary embodiment 500 of a node of a neural network is illustrated. A node may include, without limitation, a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 6:
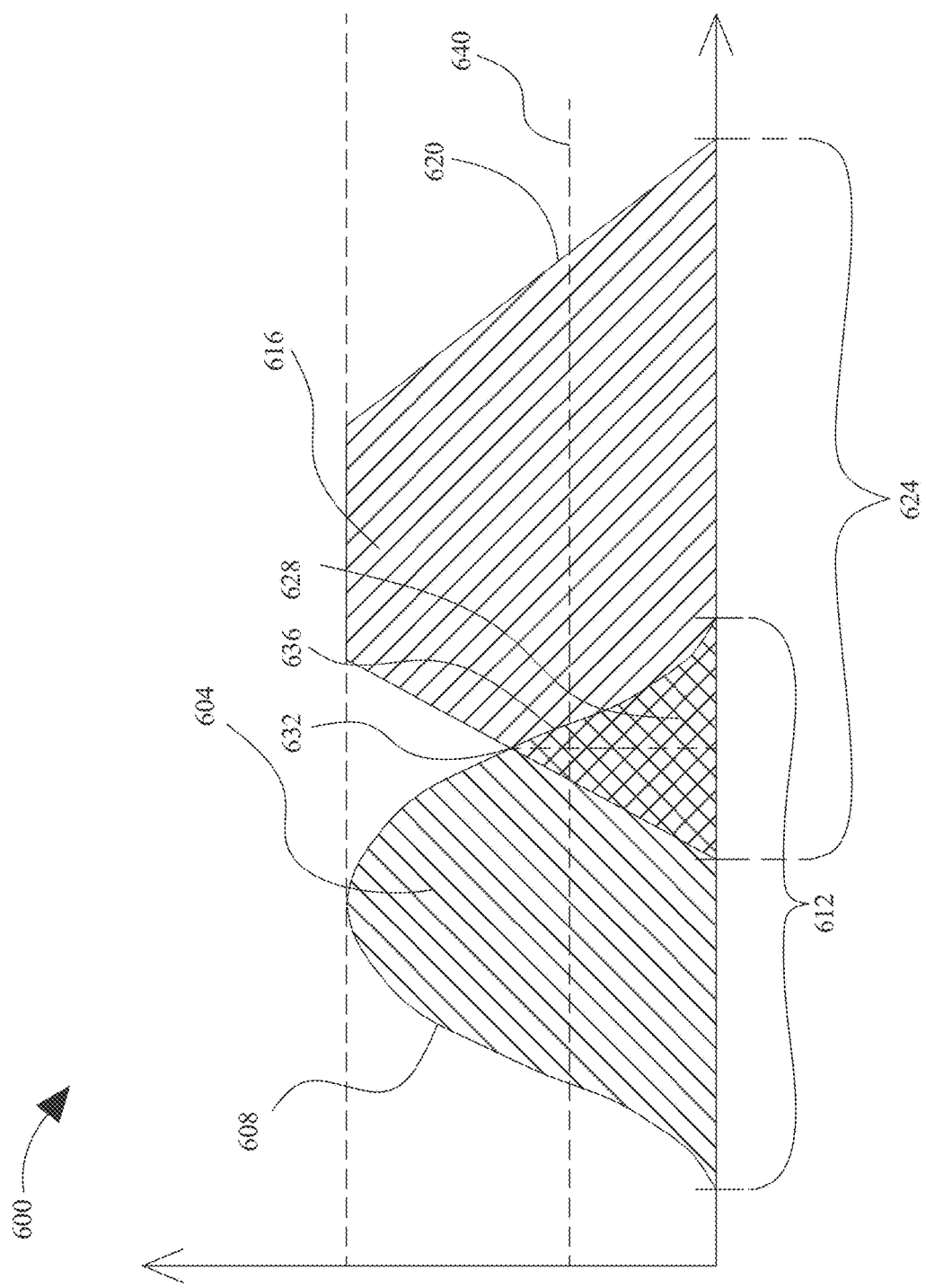
FIG. 6 is an illustration of an exemplary embodiment of fuzzy set comparison.

Now referring to FIG. 6, an exemplary embodiment of fuzzy set comparison 600 is illustrated. In a non-limiting embodiment, the fuzzy set comparison. In a non-limiting embodiment, fuzzy set comparison 600 may be consistent with fuzzy set comparison in FIGS. 1A-D. In another non-limiting the fuzzy set comparison 600 may be consistent with the name/version matching as described herein. For example and without limitation, the parameters, weights, and/or coefficients of the membership functions may be tuned using any machine-learning methods for the name/version matching as described herein. In another non-limiting embodiment, the fuzzy set may represent examples of testing data 124 and examples of textual data 132 from FIGS. 1A-D.

Alternatively or additionally, and still referring to FIG. 6, fuzzy set comparison 600 may be generated as a function of determining the data compatibility threshold. The compatibility threshold may be determined by a computing device. In some embodiments, a computing device may use a logic comparison program, such as, but not limited to, a fuzzy logic model to determine the compatibility threshold and/or version authenticator. Each such compatibility threshold may be represented as a value for a posting variable representing the compatibility threshold, or in other words a fuzzy set as described above that corresponds to a degree of compatibility and/or allowability as calculated using any statistical, machine-learning, or other method that may occur to a person skilled in the art upon reviewing the entirety of this disclosure. In some embodiments, determining the compatibility threshold and/or version authenticator may include using a linear regression model. A linear regression model may include a machine learning model. A linear regression model may map statistics such as, but not limited to, frequency of the same range of version numbers, and the like, to the compatibility threshold and/or version authenticator. In some embodiments, determining the compatibility threshold of any posting may include using a classification model. A classification model may be configured to input collected data and cluster data to a centroid based on, but not limited to, frequency of appearance of the range of versioning numbers, linguistic indicators of compatibility and/or allowability, and the like. Centroids may include scores assigned to them such that the compatibility threshold may each be assigned a score. In some embodiments, a classification model may include a K-means clustering model. In some embodiments, a classification model may include a particle swarm optimization model. In some embodiments, determining a compatibility threshold may include using a fuzzy inference engine. A fuzzy inference engine may be configured to map one or more compatibility threshold using fuzzy logic. In some embodiments, a plurality of computing devices may be arranged by a logic comparison program into compatibility arrangements. A "compatibility arrangement" as used in this disclosure is any grouping of objects and/or data based on skill level and/or output score. Membership function coefficients and/or constants as described above may be tuned according to classification and/or clustering algorithms. For instance, and without limitation, a clustering algorithm may determine a Gaussian or other distribution of questions about a centroid corresponding to a given compatibility threshold and/or version authenticator, and an iterative or other method may be used to find a membership function, for any membership function type as described above, that minimizes an average error from the statistically determined distribution, such that, for instance, a triangular or Gaussian membership function about a centroid representing a center of the distribution that most closely matches the distribution. Error functions to be minimized, and/or methods of minimization, may be performed without limitation according to any error function and/or error function minimization process and/or method as described in this disclosure.

Still referring to FIG. 6, inference engine may be implemented according to input examples of testing data 124 and examples of textual data 132. For instance, an acceptance variable may represent a first measurable value pertaining to the classification of examples of testing data 124 to examples of textual data 132. Continuing the example, an output variable may represent textual data 132 associated with a medical test. In an embodiment, examples of testing data 124 and/or examples of textual data 132 may be represented by their own fuzzy set. In other embodiments, the classification of the data into textual data 132 may be represented as a function of the intersection two fuzzy sets as shown in FIG. 6, An inference engine may combine rules, such as any semantic versioning, semantic language, version ranges, and the like thereof. The degree to which a given input function membership matches a given rule may be determined by a triangular norm or "T-norm" of the rule or output function with the input function, such as min (a, b), product of a and b, drastic product of a and b, Hamacher product of a and b, or the like, satisfying the rules of commutativity (T(a, b)=T(b, a)), monotonicity: (T(a, b)≤T (c, d) if a≤c and b≤d), (associativity: T(a, T(b, c))=T(T(a, b), c)), and the requirement that the number 1 acts as an identity element. Combinations of rules ("and" or "or" combination of rule membership determinations) may be performed using any T-conorm, as represented by an inverted T symbol or "⊥," such as max (a, b), probabilistic sum of a and b (a+b−a*b), bounded sum, and/or drastic T-conorm; any T-conorm may be used that satisfies the properties of commutativity: ⊥(a, b)=⊥(b, a), monotonicity: ⊥(a, b)≤⊥(c, d) if a≤c and b≤d, associativity: ⊥(a, ⊥(b, c))=⊥(⊥(a, b), c), and identity element of 0. Alternatively or additionally T-conorm may be approximated by sum, as in a "product-sum" inference engine in which T-norm is product and T-conorm is sum. A final output score or other fuzzy inference output may be determined from an output membership function as described above using any suitable defuzzification process, including without limitation Mean of Max defuzzification, Centroid of Area/Center of Gravity defuzzification, Center Average defuzzification, Bisector of Area defuzzification, or the like. Alternatively or additionally, output rules may be replaced with functions according to the Takagi-Sugeno-King (TSK) fuzzy model.

A first fuzzy set 604 may be represented, without limitation, according to a first membership function 608 representing a probability that an input falling on a first range of values 612 is a member of the first fuzzy set 604, where the first membership function 608 has values on a range of probabilities such as without limitation the interval [0,1], and an area beneath the first membership function 608 may represent a set of values within first fuzzy set 604. Although first range of values 612 is illustrated for clarity in this exemplary depiction as a range on a single number line or axis, first range of values 612 may be defined on two or more dimensions, representing, for instance, a Cartesian product between a plurality of ranges, curves, axes, spaces, dimensions, or the like. First membership function 608 may include any suitable function mapping first range of values 612 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, \text{ for } x > c \text{ and } x < a \\ \frac{x-a}{b-a}, \text{ for } a \leq x < b \\ \frac{c-x}{c-b}, \text{ if } b < x \leq c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

First fuzzy set 604 may represent any value or combination of values as described above, including any examples of testing data 124 and examples of textual data 132. A second fuzzy set 616, which may represent any value which may be represented by first fuzzy set 604, may be defined by a second membership function 620 on a second range 624; second range 624 may be identical and/or overlap with first range of values 612 and/or may be combined with first range via Cartesian product or the like to generate a mapping permitting evaluation overlap of first fuzzy set 604 and second fuzzy set 616. Where first fuzzy set 604 and second fuzzy set 616 have a region 636 that overlaps, first membership function 608 and second membership function 620 may intersect at a point 632 representing a probability, as defined on probability interval, of a match between first fuzzy set 604 and second fuzzy set 616. Alternatively or additionally, a single value of first and/or second fuzzy set may be located at a locus on first range of values 612 and/or second range 624, where a probability of membership may be taken by evaluation of first membership function 608 and/or second membership function 620 at that range point. A probability at 628 and/or 632 may be compared to a threshold 640 to determine whether a positive match is indicated. Threshold 640 may, in a non-limiting example, represent a degree of match between first fuzzy set 604 and second fuzzy set 616, and/or single values therein with each other or with either set, which is sufficient for purposes of the matching process; for instance, the classification into one or more query categories may indicate a sufficient degree of overlap with fuzzy set representing examples of testing data 124 and examples of textual data 132 for combination to occur as described above. Each threshold may be established by one or more user inputs. Alternatively or additionally, each threshold may be tuned by a machine-learning and/or statistical process, for instance and without limitation as described in further detail below.

In an embodiment, a degree of match between fuzzy sets may be used to rank one resource against another. For instance, if both examples of testing data 124 and examples of textual data 132 have fuzzy sets, textual data 132 may be generated by having a degree of overlap exceeding a predictive threshold, processor 104 may further rank the two resources by ranking a resource having a higher degree of match more highly than a resource having a lower degree of match. Where multiple fuzzy matches are performed, degrees of match for each respective fuzzy set may be computed and aggregated through, for instance, addition, averaging, or the like, to determine an overall degree of match, which may be used to rank resources; selection between two or more matching resources may be performed by selection of a highest-ranking resource, and/or multiple notifications may be presented to a user in order of ranking.

Figure 7:
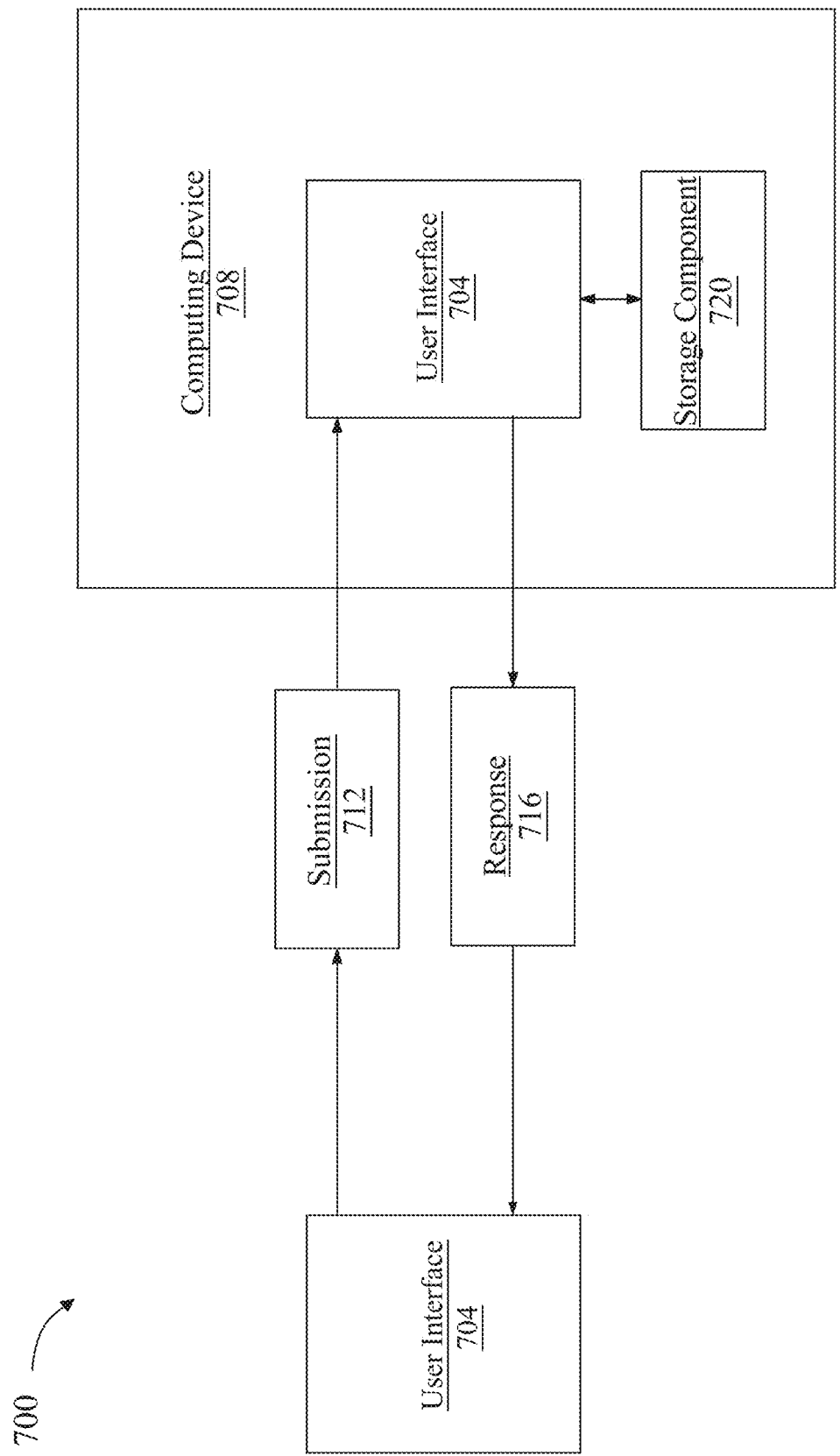
FIG. 7 is an illustration of an exemplary embodiment of a chatbot.

Referring to FIG. 7, a chatbot system 700 is schematically illustrated. According to some embodiments, a user interface 704 may be communicative with a computing device 708 that is configured to operate a chatbot. In some cases, user interface 704 may be local to computing device 708. Alternatively or additionally, in some cases, user interface 704 may remote to computing device 708 and communicative with the computing device 708, by way of one or more networks, such as without limitation the internet. Alternatively or additionally, user interface 704 may communicate with user device using telephonic devices and networks, such as without limitation fax machines, short message service (SMS), or multimedia message service (MMS). Commonly, user interface 704 communicates with computing device 708 using text-based communication, for example without limitation using a character encoding protocol, such as American Standard for Information Interchange (ASCII). Typically, a user interface 704 conversationally interfaces a chatbot, by way of at least a submission 712, from the user interface 704 to the chatbot, and a response 716, from the chatbot to the user interface 704. In many cases, one or both submission 712 and response 716 are text-based communication. Alternatively or additionally, in some cases, one or both of submission 712 and response 716 are audio-based communication.

Continuing in reference to FIG. 7, a submission 712 once received by computing device 708 operating a chatbot, may be processed by a processor. In some embodiments, processor processes a submission 712 using one or more keyword recognition, pattern matching, and natural language processing. In some embodiments, processor employs real-time learning with evolutionary algorithms. In some cases, processor may retrieve a pre-prepared response from at least a storage component 720, based upon submission 712. Alternatively or additionally, in some embodiments, processor communicates a response 716 without first receiving a submission 712, thereby initiating conversation. In some cases, processor communicates an inquiry to user interface 704; and the processor is configured to process an answer to the inquiry in a following submission 712 from the user interface 704. In some cases, an answer to an inquiry present within a submission 712 from a user device may be used by computing device 708 as an input to another function.

With continued reference to FIG. 7, A chatbot may be configured to provide a user with a plurality of options as an input into the chatbot. Chatbot entries may include multiple choice, short answer response, true or false responses, and the like. A user may decide on what type of chatbot entries are appropriate. In some embodiments, the chatbot may be configured to allow the user to input a freeform response into the chatbot. The chatbot may then use a decision tree, data base, or other data structure to respond to the users entry into the chatbot as a function of a chatbot input. As used in the current disclosure, "Chatbot input" is any response that a candidate or employer inputs in to a chatbot as a response to a prompt or question.

With continuing reference to FIG. 7, computing device 708 may be configured to the respond to a chatbot input using a decision tree. A "decision tree," as used in this disclosure, is a data structure that represents and combines one or more determinations or other computations based on and/or concerning data provided thereto, as well as earlier such determinations or calculations, as nodes of a tree data structure where inputs of some nodes are connected to outputs of others. Decision tree may have at least a root node, or node that receives data input to the decision tree, corresponding to at least a candidate input into a chatbot. Decision tree has at least a terminal node, which may alternatively or additionally be referred to herein as a "leaf node," corresponding to at least an exit indication; in other words, decision and/or determinations produced by decision tree may be output at the at least a terminal node. Decision tree may include one or more internal nodes, defined as nodes connecting outputs of root nodes to inputs of terminal nodes. Computing device 708 may generate two or more decision trees, which may overlap; for instance, a root node of one tree may connect to and/or receive output from one or more terminal nodes of another tree, intermediate nodes of one tree may be shared with another tree, or the like.

Still referring to FIG. 7, computing device 708 may build decision tree by following relational identification; for example, relational indication may specify that a first rule module receives an input from at least a second rule module and generates an output to at least a third rule module, and so forth, which may indicate to computing device 708 an in which such rule modules will be placed in decision tree. Building decision tree may include recursively performing mapping of execution results output by one tree and/or subtree to root nodes of another tree and/or subtree, for instance by using such execution results as execution parameters of a subtree. In this manner, computing device 708 may generate connections and/or combinations of one or more trees to one another to define overlaps and/or combinations into larger trees and/or combinations thereof. Such connections and/or combinations may be displayed by visual interface to user, for instance in first view, to enable viewing, editing, selection, and/or deletion by user; connections and/or combinations generated thereby may be highlighted, for instance using a different color, a label, and/or other form of emphasis aiding in identification by a user. In some embodiments, subtrees, previously constructed trees, and/or entire data structures may be represented and/or converted to rule modules, with graphical models representing them, and which may then be used in further iterations or steps of generation of decision tree and/or data structure. Alternatively or additionally subtrees, previously constructed trees, and/or entire data structures may be converted to APIs to interface with further iterations or steps of methods as described in this disclosure. As a further example, such subtrees, previously constructed trees, and/or entire data structures may become remote resources to which further iterations or steps of data structures and/or decision trees may transmit data and from which further iterations or steps of generation of data structure receive data, for instance as part of a decision in a given decision tree node.

Continuing to refer to FIG. 7, decision tree may incorporate one or more manually entered or otherwise provided decision criteria. Decision tree may incorporate one or more decision criteria using an application programmer interface (API). Decision tree may establish a link to a remote decision module, device, system, or the like. Decision tree may perform one or more database lookups and/or look-up table lookups. Decision tree may include at least a decision calculation module, which may be imported via an API, by incorporation of a program module in source code, executable, or other form, and/or linked to a given node by establishing a communication interface with one or more exterior processes, programs, systems, remote devices, or the like; for instance, where a user operating system has a previously existent calculation and/or decision engine configured to make a decision corresponding to a given node, for instance and without limitation using one or more elements of domain knowledge, by receiving an input and producing an output representing a decision, a node may be configured to provide data to the input and receive the output representing the decision, based upon which the node may perform its decision.

Figure 8:
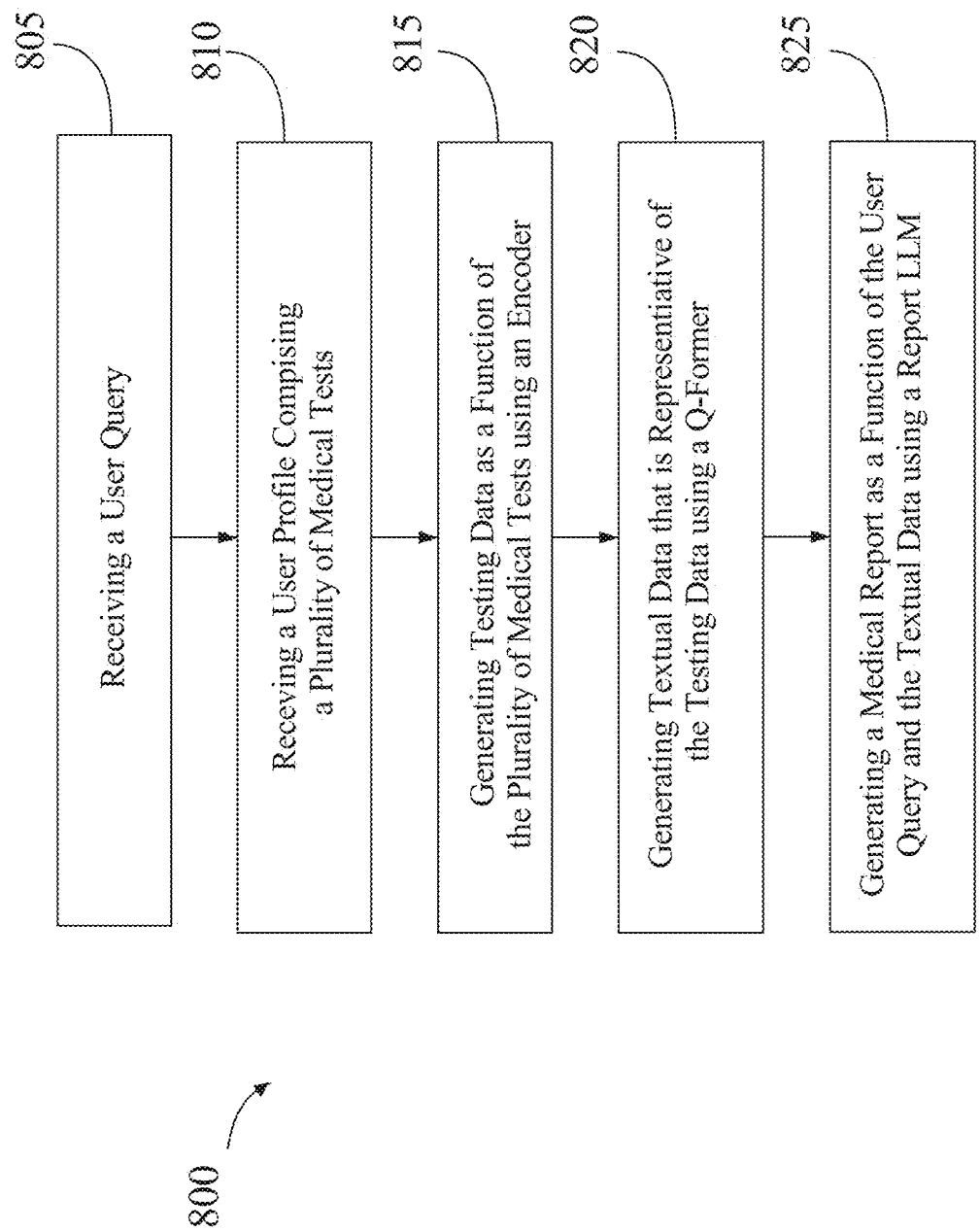
FIG. 8 is a flow diagram of an exemplary method for the generation of a medical report.

Referring now to FIG. 8, a flow diagram of an exemplary method 800 for the generation of a medical report is illustrated. At step 805, method 800 includes receiving, using at least a processor, a user query. This may be implemented as described and with reference to FIGS. 1-7. In some cases, the method may include generating contextual data as a function of the user profile. In an embodiment, receiving the user profile may include receiving the user profile from one or more electronic health records.

Still referring to FIG. 8, at step 810, method 800 includes receiving, using the at least a processor, a user profile comprising a plurality of medical tests. This may be implemented as described and with reference to FIGS. 1-7.

Still referring to FIG. 8, at step 815, method 800 includes generating, using the at least a processor, testing data as a function of the plurality of medical tests using an encoder. This may be implemented as described and with reference to FIGS. 1-7. In an embodiment, the encoder may include a frozen encoder; and the report LLM comprises a frozen report LLM and an iteratively trained report LLM.

Still referring to FIG. 8, at step 820, method 800 includes generating, using the at least a processor, textual data that is representative of the testing data using a querying transformer model (Q-former). Generating the textual data comprises iteratively training the Q-former using transformer training data, wherein transformer training data comprises examples of testing data as inputs correlated to examples of textual data as outputs. Additionally, generating the textual data comprises generating the textual data using the trained querying transformer model. This may be implemented as described and with reference to FIGS. 1-7. In an embodiment, wherein generating the medical report comprises iteratively training the report LLM using one or more reinforcement learning techniques and/or one or more direct preference optimization techniques. In another embodiment, iteratively training the Q-former further comprises triggering a back-propagation mechanism as a function of the medical report. In a third embodiment, iteratively training the Q-former further may include receiving pairs of transformer training data, wherein the pairs of transformer training data comprises at least one example of testing data paired with at least one example of textual data that corresponds to the example of testing data. Training the Q-former further may include generating an embedding for each pair of transformer training data, wherein generating the embeddings comprises transforming each pair of transformer training data into a unified vector space. Training the Q-former further may include applying a plurality of loss functions to each embedding of a plurality of embeddings.

Still referring to FIG. 8, at step 825, method 800 includes generating, using the at least a processor, a medical report as a function of the user query and the textual data using a report large language model (LLM). This may be implemented as described and with reference to FIGS. 1-7. In an embodiment, the medical report comprises an electrocardiogram report and/or an echocardiogram report.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
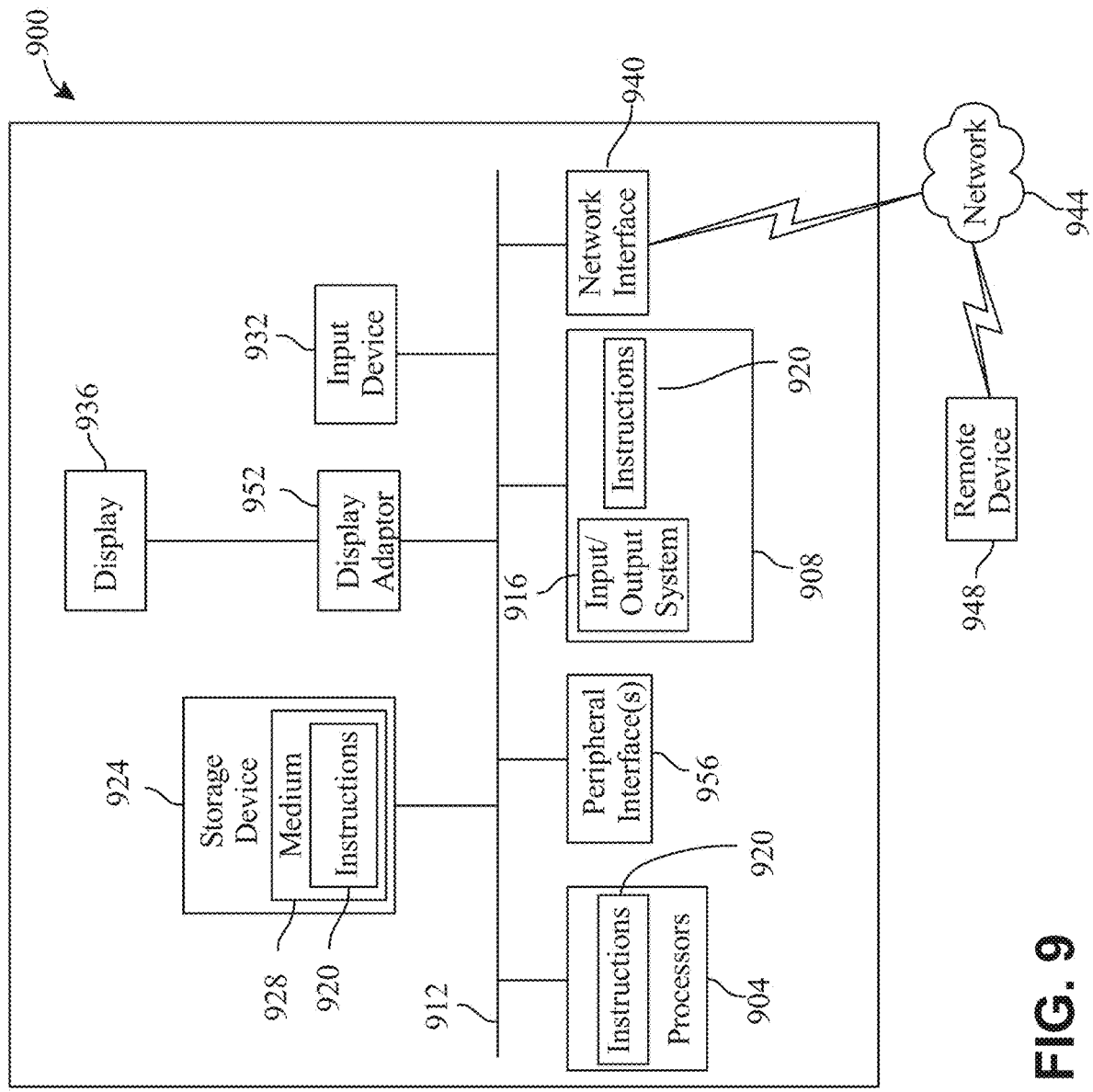
FIG. 9 is a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Processor 904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIREWIRE interface, a direct interface to bus 912, and any combinations thereof. Input device 932 may include a touch screen interface that may be a part of or separate from display device 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. An apparatus for generation of a medical report, wherein the apparatus comprises:
   at least a processor; and
   a memory communicatively connected to the at least a processor, wherein the memory contains instructions configuring the at least a processor to:
      receive a user query corresponding to a user;
      receive a user profile comprising a plurality of medical tests associated with the user, wherein the plurality of medical tests comprise one or more various data types;
      generate testing data as a function of the plurality of medical tests using an encoder;
      generate textual data that is representative of the testing data using a querying transformer model (Q-former), wherein the textual data is mapped wherein generating the textual data comprises:
         training the Q-former using transformer training data, wherein transformer training data comprises pairs of examples of testing data as inputs and examples of textual data; and
         generating, as an output, the textual data using the trained querying transformer model, wherein the textual data comprises one or more embeddings configured to reduce a dimensionality of the testing data and mapped within a unified vector space, wherein the one or more embeddings correspond to the one or more various data types; and
      generate a medical report as a function of the user query and the output of the trained querying transformer model using a report large language model (LLM).

2. The apparatus of claim 1, wherein the medical report comprises an electrocardiogram report.

3. The apparatus of claim 1, wherein the medical report comprises an echocardiogram report.

4. The apparatus of claim 1, wherein receiving the user query comprises receiving the user query using a chatbot.

5. The apparatus of claim 1, wherein generating the medical report comprises initially training the report LLM using instruction fine-tuning techniques and subsequently optimizing the report LLM using one or more reinforcement learning techniques.

6. The apparatus of claim 1, wherein generating the medical report comprises training the report LLM using one or more direct preference optimization techniques.

7. The apparatus of claim 1, wherein memory further instructs the processor to generate contextual data as a function of the user profile.

8. The apparatus of claim 1, wherein training the Q-former further comprises using a back-propagation mechanism to update weights of the Q-former as a function of the report LLM.

9. The apparatus of claim 1, wherein training the Q-former further comprises:
   receiving pairs of transformer training data, wherein the pairs of transformer training data comprises at least one example of testing data paired with at least one example of textual data that corresponds to the example of testing data;
   generating an embedding for each pair of transformer training data, wherein generating the embeddings comprises transforming each pair of transformer training data into a unified vector space; and
   applying a plurality of loss functions to each embedding of a plurality of embeddings.

10. The apparatus of claim 1, wherein receiving the user profile comprises receiving the user profile from one or more electronic health records.

11. A method for generation of a medical report, wherein the method comprises:
- receiving, using at least a processor, a user query corresponding to a user;
- receiving, using the at least a processor, a user profile comprising a plurality of medical tests associated with the user, wherein the plurality of medical tests comprise one or more various data types;
- generating, using the at least a processor, testing data as a function of the plurality of medical tests using an encoder;
- generating, using the at least a processor, textual data that is representative of the testing data using a querying transformer model (Q-former), wherein generating the textual data comprises:
  - training the Q-former using transformer training data, wherein transformer training data comprises pairs of examples of testing data and examples of textual data; and
  - generating, as an output, the textual data using the trained querying transformer model, wherein the textual data comprises one or more embeddings configured to reduce a dimensionality of the testing data and mapped within a unified vector space, wherein the one or more embeddings correspond to the one or more various data types; and
- generating, using the at least a processor, a medical report as a function of the user query and the and the output of the trained querying transformer model using a report large language model (LLM).

12. The method of claim 11, wherein the medical report comprises an electrocardiogram report.

13. The method of claim 11, wherein the medical report comprises an echocardiogram report.

14. The method of claim 11, wherein receiving the user query comprises receiving the user query using a chatbot.

15. The method of claim 11, wherein generating the medical report comprises iteratively training the report LLM using one or more reinforcement learning techniques.

16. The method of claim 11, wherein generating the medical report comprises iteratively training the report LLM using one or more direct preference optimization techniques.

17. The method of claim 11, wherein the method further comprises generating, using the at least a processor, contextual data as a function of the user profile.

18. The method of claim 11, wherein iteratively training the Q-former further comprises triggering a back-propagation mechanism as a function of the medical report.

19. The method of claim 11, wherein iteratively training the Q-former comprises:
- receiving pairs of transformer training data, wherein the pairs of transformer training data comprises at least one example of testing data paired with at least one example of textual data that corresponds to the example of testing data:
- generating an embedding for each pair of transformer training data, wherein generating the embeddings comprises transforming each pair of transformer training data into a unified vector space; and
- applying a plurality of loss functions to each embedding of a plurality of embeddings.

20. The method of claim 11, wherein receiving the user profile comprises receiving the user profile from one or more electronic health records.

* * * * *